United States Patent
Goldfarb

(10) Patent No.: US 8,642,660 B2
(45) Date of Patent: Feb. 4, 2014

(54) METHOD FOR ALTERING THE LIFESPAN OF EUKARYOTIC ORGANISMS

(75) Inventor: David Scott Goldfarb, Mendon, NY (US)

(73) Assignee: The University of Rochester, Rochester, NY (US)

( * ) Notice: Subject to any disclaimer, the term of this patent is extended or adjusted under 35 U.S.C. 154(b) by 981 days.

(21) Appl. No.: 12/341,615

(22) Filed: Dec. 22, 2008

(65) Prior Publication Data

US 2009/0163545 A1 Jun. 25, 2009

Related U.S. Application Data

(60) Provisional application No. 61/016,362, filed on Dec. 21, 2007, provisional application No. 61/023,801, filed on Jan. 25, 2008.

(51) Int. Cl.
*A61K 31/122* (2006.01)
*A61K 31/47* (2006.01)

(52) U.S. Cl.
USPC ............ 514/641; 514/312; 514/688; 514/2

(58) Field of Classification Search
USPC .................................... 514/312, 688, 614, 2
See application file for complete search history.

(56) References Cited

U.S. PATENT DOCUMENTS

| | | |
|---|---|---|
| 2004/0265861 A1 | 12/2004 | Goldfarb |
| 2005/0096256 A1 | 5/2005 | Sinclair |
| 2010/0227936 A1 | 9/2010 | Moran et al. |

FOREIGN PATENT DOCUMENTS

| | | |
|---|---|---|
| EP | 0017195 A1 | 10/1980 |
| JP | 5640634 A | 4/1981 |
| WO | 2006021743 A1 | 3/2006 |
| WO | 2006090177 A1 | 8/2006 |

OTHER PUBLICATIONS

Le Couteur et al (J Gerontol A Biol Sci Med Sci. Feb. 2012;67A(2):168-174.*
Jazwinski (Journal of Gerontology 45(3)B68-74, 1990.*
Minois et al., Ageing Research Reviews 5:52-59, 2006.*
Anderson, Chem and Biol 10:787-797, 2003.*
Thiel, Nature Biotechnol 2:513-519, 2004.*
Marmorstein; Structure and chemistry of the Sir2 family of NAD+-dependent histone/protein deactylases; Biochemical Society Transactions, 2004, vol. 32, Part 6; pp. 904-909.
CID 6389534; Compound Summary; Create Date Sep. 17, 2005. [Retrieved from the Internet Apr. 21, 2009: <http://pubchem.ncbi.nlm.nih.gov/summary/summary.cgi?cid=6389534&loc=ec_rcs>].
CID 17402577; Compound Summary; Create Date Nov. 13, 2007. [Retrieved from the Internet Apr. 21, 2009: <http://pubchem.ncbi.nlm.nih.gov/summary/summary.cgi?cid=17402577&loc=ec_rcs>].
Kaeberlein et al.; Sir2-Independent Life Span Extension by Calorie Restriction in Yeast; PLOS Biology, Sep. 2004, vol. 2, Issue 9, e296; pp. 1381-1387.
Smith et al.; Genome-wide identification of conserved longevity genes in yeast and worms; Mechanisms of Ageing and Development, 2007, vol. 128; pp. 106-111.

(Continued)

*Primary Examiner* — Savitha Rao
(74) *Attorney, Agent, or Firm* — Ropes & Gray LLP

(57) ABSTRACT

A method for altering the lifespan of a eukaryotic organism. The method comprises the steps of providing a lifespan altering compound, and administering an effective amount of the compound to a eukaryotic organism, such that the lifespan of the organism is altered. In one embodiment, the compound is identified using the DeaD assay.

1 Claim, 47 Drawing Sheets

A.

B.

(56) References Cited

OTHER PUBLICATIONS

Howitz et al.; Small molecule activators of sirtuins extend *Saccharomyces cerevisiae* lifespan; Nature, Sep. 11, 2003, vol. 425; pp. 191-196.

Anderson et al.; Nicotinamide and PNC1 govern lifespan extension by calorie restriction in *Saccharomyces cerevisiae;* Nature, May 8, 2003, vol. 423; pp. 181-185.

Kaeberlein et al.; Recent Developments in Yeast Aging; PLOS Genetics, May 2007, vol. 3, Issue 5, e84; pp. 0655-0660.

Bitterman et al.; Longevity Regulation in *Saccharomyces cerevisiae:* Linking Metabolism, Genome Stability, and Heterochromatin; Microbiology and Molecular Biology Reviews, Sep. 2003, vol. 67, No. 3; pp. 376-399.

Yang et al.; NAD Metabolism and Sirtuins: Metabolic Regulation of Protein Deacetylation in Stress and Toxicity; The AAPS Journal 2006, vol. 8, No. 4, Article 72; pp. E632-E643.

Petrascheck et al.; An Antidepressant that extends lifespan in adult *Caenorhabditis elegans;* Nature, Nov. 22, 2007, vol. 450; doi:10.1038/nature05991; pp. 553-557.

Tsuchiya et al.; Sirtuin-independent effects of nicotinamide on lifespan extension from calorie restriction in yeast; Aging Cell, 2006, vol. 5; pp. 505-514.

Al-Dhalimy et al.; Long-Term Therapy with NTBC and Tyrosine-Restricted Diet in a Murine Model of Hereditary Tyrosinemia Type I; Molecular Genetics and Metabolism, 2002, vol. 75; pp. 38-45.

\* cited by examiner

| Cluster based on | # | Scaffold |
|---|---|---|
| High activity hits | c1 | (scaffold structure) |
| | c2 | (scaffold structure) |
| | c3 | (scaffold structure) |

Figure 6A.

| Cluster based on | # | Scaffold |
|---|---|---|
| Low activity hits | cc1 | (scaffold structure) |
| | cc2 | (scaffold structure with [C,N,O] label) |
| | cc3a | (scaffold structure) |

Figure 6B.

| Cluster based on | # | Scaffold |
|---|---|---|
| Low activity hits | cc3b | 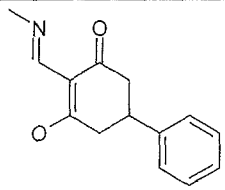 |
| | cc4 | 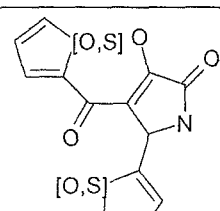 |
| | cc5 | 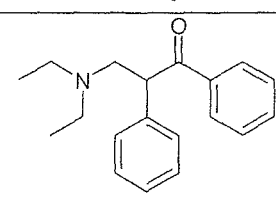 |
| | cc6 | 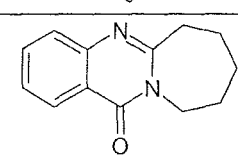 |
| | cc7 | 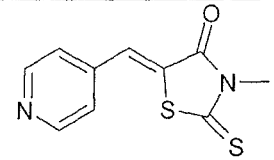 |
| | cc8 | 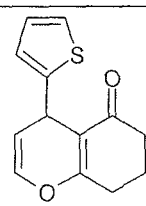 |
Figure 6C.

Table 1

| No. | PubChem SID | % Activation @ 10 uM, No NAM | % Activation @ 5 uM, No NAM | % Activation @ 2.5 uM, No NAM | % Activation @ 1.25 uM, No NAM | EC50, No NAM | EC50 Curve Status, No NAM | EC50, with NAM | EC50 Curve Status, with NAM |
|---|---|---|---|---|---|---|---|---|---|
| 1 | 17402577 | 17.68 | 8.94 | 15.2 | 20.25 | >40 | Inactive | <0.078 | Active |
| 2 | 4245630 | 19.32 | 16.05 | 11.02 | 22.28 | >40 | Inactive | <0.078 | Active |
| 3 | 16953124 | 20.77 | 22.31 | 20.29 | 18.86 | >40 | Inactive | <0.078 | Active |
| 4 | 4251887 | 7.56 | 11.06 | 3.89 | 9.26 | >40 | Inactive | 0.24 | Active |
| 5 | 22400413 | 27.49 | 18.54 | 28.21 | 18.52 | >40 | Inactive | 0.58 | Active |
| 6 | 17402574 | 11.11 | 9.31 | -4.15 | 4.72 | >40 | Inactive | 0.63 | Active |
| 7 | 17507366 | 17.23 | 17.82 | 16.61 | 18.21 | >40 | Inactive | 1.07 | Active |
| 8 | 857671 | 31.51 | 31.71 | 30.57 | 27.16 | <0.078 | Inconclusive | 1.12 | Active |
| 9 | 4263828 | 20.29 | 15.89 | 6.23 | 9.92 | >40 | Inactive | 1.13 | Active |
| 10 | 862076 | 0 | 0.65 | -0.84 | -8.79 | >40 | Inactive | 1.14 | Active |
| 11 | 4245922 | 18.49 | 9.76 | -0.17 | 1.88 | >40 | Inactive | 1.2 | Active |
| 12 | 17512647 | 21.38 | 9.92 | 12.33 | 12.4 | >40 | Inactive | 1.2 | Active |
| 13 | 4250971 | 29.47 | 20.87 | 12.94 | 23.09 | >40 | Inactive | 1.42 | Active |
| 14 | 7978235 | 19.77 | 14.15 | 9.97 | 18.21 | >40 | Inactive | 1.67 | Active |
| 15 | 847157 | 10.13 | 5.2 | -5.41 | 2.2 | >40 | Inactive | 1.7 | Active |
| 16 | 22413972 | 11.27 | 8.51 | 5.27 | 10.57 | >40 | Inactive | 1.72 | Active |
| 17 | 7965978 | -0.96 | 0.65 | -4.56 | 0.47 | >40 | Inactive | 1.75 | Active |
| 18 | 17510022 | -9.32 | -4.72 | -6.76 | -0.94 | >40 | Inactive | 1.79 | Active |
| 19 | 14734026 | 1.45 | -6.34 | -5.41 | -3.45 | >40 | Inactive | 1.98 | Active |
| 20 | 14743053 | 21.86 | 7.48 | 1.35 | 8.79 | >40 | Inactive | 1.99 | Active |
| 21 | 14724551 | 24.28 | 10.57 | 22.3 | 8.48 | >40 | Inactive | 2.06 | Active |
| 22 | 17505716 | 5.64 | 9.31 | 4.47 | 5.2 | >40 | Inactive | 2.08 | Active |
| 23 | 22401805 | 11.59 | 14.77 | 7.51 | 9.11 | >40 | Inactive | 2.22 | Active |
| 24 | 17415346 | 14.95 | 19.19 | 8.95 | 20.72 | >40 | Inactive | 2.24 | Active |
| 25 | 14732512 | 21.7 | 12.85 | 12.33 | 2.35 | >40 | Inactive | 2.33 | Active |
| 26 | 17512049 | 14.17 | 14.77 | 15.5 | 4.55 | >40 | Inactive | 2.55 | Active |
| 27 | 14733039 | 31.56 | 26.97 |  | 21.3 | >40 | Inactive | 2.64 | Active |
| 28 | 14730554 | 10.14 | 6.1 | 3.35 | -0.16 | >40 | Inactive | 2.75 | Active |
| 29 | 22412422 | 22.67 | 15.45 | 6.08 | 18.84 | >40 | Inactive | 2.84 | Active |
| 30 | 17402008 | 23.15 | 18.37 | -2.53 | 12.72 | >40 | Inactive | 2.9 | Active |
| 31 | 17411197 | 29.74 | 11.71 | 17.57 | 25.75 | >40 | Inactive | 2.94 | Active |
| 32 | 842207 | 11.9 | 6.02 | 1.69 | 9.89 | >40 | Inactive | 3.01 | Active |
| 33 | 4249431 | 5.31 | 1.14 | 15.03 | -0.16 | >40 | Inactive | 3.02 | Active |
| 34 | 17511154 | 9.18 | 2.09 | 3.35 | 0.81 | >40 | Inactive | 3.02 | Active |
| 35 | 17508428 | 13.18 | 15.12 | 10.3 | 2.51 | >40 | Inactive | 3.11 | Active |
| 36 | 3712052 | 7.73 | 12.04 | 14.06 | 6.34 | >40 | Inactive | 3.15 | Active |
| 37 | 17507466 | 30.23 | 17.24 | 9.29 | 13.66 | >40 | Inactive | 3.17 | Active |
| 38 | 3717077 | 13.67 | 13.17 | -0.17 | 0.47 | >40 | Inactive | 3.18 | Active |
| 39 | 17506345 | 8.21 | 5.78 | -0.96 | -4.72 | >40 | Inactive | 3.19 | Active |
| 40 | 22413395 | 8.36 | 5.53 | 1.01 | 2.98 | >40 | Inactive | 3.21 | Active |
| 41 | 22402211 | 5.8 | 0.64 | 4.95 | -2.11 | >40 | Inactive | 3.21 | Active |
| 42 | 17514347 | 6.44 | 12.2 | 11.82 | 5.53 | >40 | Inactive | 3.26 | Active |
| 43 | 17510032 | 7.23 | 4.39 | 0.17 | -0.94 | >40 | Inactive | 3.28 | Active |
| 44 | 17510012 | 16.56 | 20.98 | 18.41 | 8.32 | >40 | Inactive | 3.28 | Active |
| 45 | 17511396 | 17.85 | 18.86 | 11.15 | 9.58 | >40 | Inactive | 3.3 | Active |
| 46 | 4241889 | -1.13 | -6.58 | 8.95 | -4.07 | >40 | Inactive | 3.32 | Active |
| 47 | 4243054 | 9.98 | 9.79 | 1.92 | 1.63 | >40 | Inactive | 3.4 | Active |
| 48 | 17511815 | 20.42 | 12.85 | 2.03 | 9.11 | >40 | Inactive | 3.53 | Active |
| 49 | 855620 | 23.51 | 15.25 | 10.86 | 9.43 | >40 | Inactive | 3.62 | Active |
| 50 | 14737835 | 9.98 | 3.05 | 5.75 | -1.63 | >40 | Inactive | 3.68 | Active |
| 51 | 14731075 | 19.94 | 9.27 | 16.22 | 9.26 | >40 | Inactive | 3.73 | Active |
| 52 | 17513297 | 15.92 | 9.92 | -4.56 | -2.51 | >40 | Inactive | 3.74 | Active |
| 53 | 17504927 | 9.97 | 2.6 | -1.52 | 0.78 | >40 | Inactive | 3.82 | Active |
| 54 | 17410710 | 7.25 | 7.38 | 4.95 | 4.39 | >40 | Inactive | 3.83 | Active |
| 55 | 17410531 | 20.58 | 23.25 | 11.15 | 4.4 | >40 | Inactive | 3.85 | Active |

Figure 16

| 56 | 22414503 | 13.34 | 4.72 | 15.03 | 4.71 | >40 | Inactive | 3.85 | Active |
|---|---|---|---|---|---|---|---|---|---|
| 57 | 4251594 | 6.59 | 1.3 | -4.22 | 1.41 | >40 | Inactive | 3.91 | Active |
| 58 | 22414623 | 24.6 | 13.5 | 25 | 20.41 | >40 | Inactive | 3.99 | Active |
| 59 | 4243100 | 11.58 | 1.63 | -5.91 | 2.83 | >40 | Inactive | 4.01 | Active |
| 60 | 7967942 | 15.76 | 11.54 | 1.52 | 10.68 | >40 | Inactive | 4.22 | Active |
| 61 | 17511447 | 20.42 | 14.96 | 15.54 | 15.86 | >40 | Inactive | 4.25 | Active |
| 62 | 17433901 | 18.97 | 21.95 | 4.05 | 6.28 | >40 | Inactive | 4.26 | Active |
| 63 | 17511642 | 17.04 | 17.24 | 24.83 | 16.01 | >40 | Inactive | 4.3 | Active |
| 64 | 847599 | 14.95 | 16.42 | -3.72 | 4.55 | >40 | Inactive | 4.31 | Active |
| 65 | 22411681 | 18.49 | 26.18 | -8.45 | 5.34 | >40 | Inactive | 4.32 | Active |
| 66 | 844675 | 4.5 | 2.76 | -1.01 | -2.2 | >40 | Inactive | 4.44 | Active |
| 67 | 17402120 | 9.5 | 10.59 | 8.63 | 2.93 | >40 | Inactive | 4.44 | Active |
| 68 | 22413469 | 17.85 | 14.96 | 9.8 | 2.83 | >40 | Inactive | 4.5 | Active |
| 69 | 17513719 | 24.92 | 23.9 | 13.68 | 16.8 | >40 | Inactive | 4.62 | Active |
| 70 | 846246 | 21.86 | | 25.51 | 5.97 | >40 | Inactive | 4.62 | Active |
| 71 | 16953263 | 14.65 | 12.36 | 3.83 | -0.33 | >40 | Inactive | 4.71 | Active |
| 72 | 17432193 | 16.1 | 17.66 | 16.45 | 6.34 | >40 | Inactive | 4.74 | Active |
| 73 | 17433800 | 15.14 | 14.93 | 13.1 | 3.74 | >40 | Inactive | 4.75 | Active |
| 74 | 22402128 | -8.7 | 0.64 | 7.67 | 10.89 | >40 | Inactive | 4.87 | Active |
| 75 | 17432366 | 8.2 | -6.99 | 3.89 | 2.2 | >40 | Inactive | 4.95 | Active |
| 76 | 22407124 | 19.94 | 18.37 | 11.82 | 9.11 | >40 | Inactive | 4.96 | Active |
| 77 | 22407084 | 20.58 | 20.98 | 10.14 | 5.02 | >40 | Inactive | 4.96 | Active |
| 78 | 17507756 | 25.88 | 11.54 | 13.34 | 5.97 | >40 | Inactive | 5.03 | Active |
| 79 | 3712184 | 21.22 | 3.41 | 2.7 | 2.35 | >40 | Inactive | 5.05 | Active |
| 80 | 17510784 | 19 | 7.87 | 1.76 | 1.3 | >40 | Inactive | 5.08 | Active |
| 81 | 22411970 | 27.17 | 19.19 | 0.68 | 14.13 | >40 | Inactive | 5.16 | Active |
| 82 | 17512537 | 9.49 | 9.92 | 7.94 | 4.87 | >40 | Inactive | 5.18 | Active |
| 83 | 14740670 | 30.27 | 17.66 | 17.09 | 13.17 | >40 | Inactive | 5.19 | Active |
| 84 | 17403258 | 7.56 | 6.67 | 5.07 | 5.97 | >40 | Inactive | 5.29 | Active |
| 85 | 17410407 | 29.95 | 20.55 | 16.61 | 8.13 | >40 | Inactive | 5.3 | Active |
| 86 | 17511910 | 6.75 | 0.16 | -3.38 | 4.08 | >40 | Inactive | 5.38 | Active |
| 87 | 17504111 | 18.81 | 9.76 | 6.08 | 0.63 | >40 | Inactive | 5.42 | Active |
| 88 | 855719 | 24.76 | 18.54 | 18.07 | 15.86 | >40 | Inactive | 5.42 | Active |
| 89 | 14744026 | 18.68 | 21.51 | 3.99 | 9.76 | >40 | Inactive | 5.46 | Active |
| 90 | 17410398 | 21.06 | 11.06 | 3.55 | 12.09 | >40 | Inactive | 5.49 | Active |
| 91 | 16953215 | 12.22 | 14.47 | 0.84 | 1.88 | >40 | Inactive | 5.51 | Active |
| 92 | 7977439 | 22.22 | 18.46 | 11.34 | 16.26 | >40 | Inactive | 5.54 | Active |
| 93 | 17410604 | 17.68 | 16.91 | 0.51 | 3.45 | >40 | Inactive | 5.62 | Active |
| 94 | 3714502 | 9.81 | 7.8 | 6.93 | 7.85 | >40 | Inactive | 5.65 | Active |
| 95 | 4265380 | 2.73 | -4.39 | -10.64 | -1.88 | >40 | Inactive | 5.71 | Active |
| 96 | 17385972 | 15.92 | 17.89 | 8.95 | 7.69 | >40 | Inactive | 5.73 | Active |
| 97 | 14723611 | 5.15 | 11.72 | 5.75 | 2.28 | >40 | Inactive | 5.73 | Active |
| 98 | 7976903 | 12.22 | 12.68 | 6.42 | 8.48 | >40 | Inactive | 5.74 | Active |
| 99 | 857535 | 18.49 | 5.85 | 12.67 | 3.61 | >40 | Inactive | 5.79 | Active |
| 100 | 4261778 | 27.7 | 34.67 | 21.73 | 20.98 | >40 | Inactive | 5.84 | Active |
| 101 | 17414658 | 4.66 | 2.6 | -3.72 | 5.65 | >40 | Inactive | 5.85 | Active |
| 102 | 17416308 | 16.08 | 10.73 | 3.55 | 13.66 | >40 | Inactive | 5.88 | Active |
| 103 | 851810 | 13.83 | 12.2 | 2.87 | 7.85 | >40 | Inactive | 5.89 | Active |
| 104 | 4250600 | 7.23 | 1.3 | -4.05 | -1.1 | >40 | Inactive | 5.89 | Active |
| 105 | 17403109 | 11.9 | 7.97 | -10.64 | 4.87 | >40 | Inactive | 5.94 | Active |
| 106 | 14742137 | 23.83 | 9.63 | 12.78 | 15.77 | >40 | Inactive | 5.95 | Active |
| 107 | 11533046 | 13.34 | 11.87 | 10.64 | 7.85 | >40 | Inactive | 5.97 | Active |
| 108 | 844441 | 9.97 | 1.79 | -3.55 | 2.35 | >40 | Inactive | 5.98 | Active |
| 109 | 7973619 | 1.61 | -3.41 | -3.21 | -4.4 | >40 | Inactive | 5.99 | Active |
| 110 | 16953120 | 8.2 | 6.83 | 9.46 | 3.61 | >40 | Inactive | 6 | Active |
| 111 | 17504924 | 9.18 | 9.15 | 2.4 | 1.63 | >40 | Inactive | 6.02 | Active |
| 112 | 22413391 | 13.5 | 15.93 | 13.85 | 1.26 | >40 | Inactive | 6.04 | Active |
| 113 | 14720421 | 21.74 | 9.31 | 9.58 | 2.93 | >40 | Inactive | 6.05 | Active |
| 114 | 22404194 | 16.08 | 17.56 | -1.35 | -0.16 | >40 | Inactive | 6.07 | Active |

Figure 16 (cont.)

| 115 | 14733148 | 2.41 | -0.33 | -3.21 | -1.1 | >40 | Inactive | 6.1 | Active |
|---|---|---|---|---|---|---|---|---|---|
| 116 | 22413392 | 25.44 | 16.21 | 1.76 | 7.32 | >40 | Inactive | 6.1 | Active |
| 117 | 17509533 | 26.89 | 19.42 | 12.14 | 10.57 | >40 | Inactive | 6.14 | Active |
| 118 | 4256720 | 6.44 | 2.89 | -5.59 | 0.33 | >40 | Inactive | 6.15 | Active |
| 119 | 14734292 | 21.06 | 16.59 | 4.56 | 4.4 | >40 | Inactive | 6.25 | Active |
| 120 | 7976920 | 3.86 | 0.98 | -11.66 | 3.45 | >40 | Inactive | 6.26 | Active |
| 121 | 850963 | 0.64 | -0.48 | -5.43 | -2.76 | >40 | Inactive | 6.32 | Active |
| 122 | 4250288 | 9.65 | 6.67 | 5.41 | 0.63 | >40 | Inactive | 6.33 | Active |
| 123 | 17386145 | 0.81 | -0.64 | -3.67 | -6.83 | >40 | Inactive | 6.34 | Active |
| 124 | 14732067 | 10.47 | 6.9 | -1.28 | 6.83 | >40 | Inactive | 6.34 | Active |
| 125 | 17403545 | 4.98 | 2.44 | 4.39 | -3.92 | >40 | Inactive | 6.35 | Active |
| 126 | 845300 | 26.69 | 19.84 | 19.76 | 17.58 | >40 | Inactive | 6.36 | Active |
| 127 | 17514054 | 19.13 | 17.07 | 4.56 | 13.81 | >40 | Inactive | 6.42 | Active |
| 128 | 7977110 | 3.7 | 7.87 | 1.76 | -2.76 | >40 | Inactive | 6.42 | Active |
| 129 | 17508284 | 8.2 | 0.16 | -3.04 | 0.16 | >40 | Inactive | 6.43 | Active |
| 130 | 22413821 | 13.99 | 8.13 | 17.57 | 4.24 | >40 | Inactive | 6.44 | Active |
| 131 | 14744820 | -2.25 | -5.14 | -14.22 | -5.85 | >40 | Inactive | 6.45 | Active |
| 132 | 865104 | 14.33 | 0.64 | -4.15 | -3.9 | >40 | Inactive | 6.46 | Active |
| 133 | 4257869 | 17.04 | 17.72 | -2.87 | 0.16 | >40 | Inactive | 6.52 | Active |
| 134 | 17510308 | 16.72 | 10.24 | 9.63 | 7.06 | >40 | Inactive | 6.52 | Active |
| 135 | 4245113 | 14.79 | -3.74 | 3.21 | -0.78 | >40 | Inactive | 6.56 | Active |
| 136 | 14720443 | 14.63 | 2.76 | 1.52 | 5.49 | >40 | Inactive | 6.59 | Active |
| 137 | 4246331 | 2.74 | 7.87 | -1.76 | -0.98 | >40 | Inactive | 6.59 | Active |
| 138 | 17386415 | 23.19 | 10.91 | -2.24 | 2.44 | >40 | Inactive | 6.59 | Active |
| 139 | 861342 | 12.54 | 4.88 | 7.94 | -0.47 | >40 | Inactive | 6.64 | Active |
| 140 | 22409797 | 10.45 | 7.32 | -7.77 | -1.73 | >40 | Inactive | 6.66 | Active |
| 141 | 17408401 | 9 | 3.25 | 4.39 | 2.98 | >40 | Inactive | 6.68 | Active |
| 142 | 22406326 | 5.47 | 1.46 | 7.94 | -6.12 | >40 | Inactive | 6.69 | Active |
| 143 | 22401657 | -7.41 | -1.93 | -6.55 | -15.28 | >40 | Inactive | 6.69 | Active |
| 144 | 17411253 | 14.47 | 1.3 | -4.05 | -2.2 | >40 | Inactive | 6.7 | Active |
| 145 | 7973189 | 4.34 | 13.98 | -2.03 | 3.3 | >40 | Inactive | 6.7 | Active |
| 146 | 7974960 | 2.09 | 7.22 | 0.64 | -4.07 | >40 | Inactive | 6.72 | Active |
| 147 | 17407462 | 6.11 | 1.3 | 2.53 | 3.92 | >40 | Inactive | 6.78 | Active |
| 148 | 14740988 | 11.09 | 11.71 | 4.05 | 3.3 | >40 | Inactive | 6.81 | Active |
| 149 | 865907 | 7.56 | 6.18 | -1.52 | -6.59 | >40 | Inactive | 6.81 | Active |
| 150 | 4242609 | 32.64 | 43.41 | 15.71 | 21.19 | 26.24 | Active | 6.84 | Active |
| 151 | 844259 | 9.65 | 8.46 | -6.76 | -12.87 | >40 | Inactive | 6.87 | Active |
| 152 | 17415263 | 1.61 | 5.04 | -7.26 | 6.12 | >40 | Inactive | 6.93 | Active |
| 153 | 22415942 | 28.66 | 16.05 | 16.13 | 14.15 | >40 | Inactive | 6.93 | Active |
| 154 | 844570 | 13.5 | 17.4 | 11.32 | 2.51 | >40 | Inactive | 6.96 | Active |
| 155 | 22416390 | 10.47 | 11.08 | -3.19 | -1.14 | >40 | Inactive | 7.01 | Active |
| 156 | 17510015 | 0.32 | 17.34 | -3.35 | 5.2 | >40 | Inactive | 7.04 | Active |
| 157 | 855762 | 10.93 | -8.13 | -2.53 | -4.71 | >40 | Inactive | 7.07 | Active |
| 158 | 861613 | 19.48 | 5.3 | 4.47 | 2.6 | >40 | Inactive | 7.09 | Active |
| 159 | 22408509 | 9.49 | 12.03 | 4.56 | 0.16 | >40 | Inactive | 7.11 | Active |
| 160 | 14734056 | 23.47 | 15.45 | 7.43 | 2.67 | >40 | Inactive | 7.11 | Active |
| 161 | 845529 | 5.31 | 2.93 | -9.97 | 0.94 | >40 | Inactive | 7.12 | Active |
| 162 | 14742928 | 4.83 | 15.57 | 2.72 | 5.53 | >40 | Inactive | 7.15 | Active |
| 163 | 4246543 | 14.81 | 1.77 | 9.11 | 18.21 | >40 | Inactive | 7.17 | Active |
| 164 | 22411663 | 5.47 | -4.88 | -0.51 | 4.24 | >40 | Inactive | 7.19 | Active |
| 165 | 4260744 | 4.66 | 4.55 | 3.38 | 10.36 | >40 | Inactive | 7.21 | Active |
| 166 | 14733333 | 14.31 | 16.1 | 17.57 | 13.81 | >40 | Inactive | 7.24 | Active |
| 167 | 22402532 | 10.61 | 7.97 | 5.24 | -1.26 | >40 | Inactive | 7.25 | Active |
| 168 | 22403758 | -2.58 | 4.65 | 1.76 | 4.55 | >40 | Inactive | 7.32 | Active |
| 169 | 22413950 | 12.7 | 4.72 | -3.55 | -0.78 | >40 | Inactive | 7.34 | Active |
| 170 | 14728967 | 30.23 | 7.15 | 7.77 | 6.12 | >40 | Inactive | 7.35 | Active |
| 171 | 22410965 | 10.29 | 1.79 | -4.05 | 1.41 | >40 | Inactive | 7.47 | Active |
| 172 | 17403143 | 9.97 | 9.92 | 11.32 | -3.77 | >40 | Inactive | 7.47 | Active |
| 173 | 14730159 | 18.65 | 16.59 | 4.39 | 13.03 | >40 | Inactive | 7.48 | Active |

Figure 16 (cont.)

| | | | | | | | | |
|---|---|---|---|---|---|---|---|---|
| 174 | 14744764 | 5.31 | 1.28 | -1.76 | -3.25 | >40 | Inactive | 7.65 | Active |
| 175 | 16953027 | 8.86 | 8.51 | -2.24 | -1.46 | >40 | Inactive | 7.66 | Active |
| 176 | 17511092 | -0.16 | -7.8 | 1.18 | -3.14 | >40 | Inactive | 7.69 | Active |
| 177 | 17516701 | -0.64 | -2.93 | -1.69 | 1.88 | >40 | Inactive | 7.75 | Active |
| 178 | 4255516 | 17.36 | 2.6 | -0.51 | 1.1 | >40 | Inactive | 7.79 | Active |
| 179 | 7974401 | 7.07 | 2.76 | -2.7 | 1.88 | >40 | Inactive | 7.82 | Active |
| 180 | 14730680 | 10.95 | 0.32 | -1.76 | -5.85 | >40 | Inactive | 7.84 | Active |
| 181 | 7971429 | 9.97 | 12.36 | 17.06 | 6.59 | >40 | Inactive | 7.85 | Active |
| 182 | 17509675 | 6.11 | 2.93 | 2.7 | 5.02 | >40 | Inactive | 7.85 | Active |
| 183 | 14729694 | 20.58 | 14.96 | 2.53 | 9.89 | >40 | Inactive | 7.92 | Active |
| 184 | 17516099 | 0.64 | 5.3 | -4.79 | -1.95 | >40 | Inactive | 7.94 | Active |
| 185 | 7976919 | 12.24 | 13.96 | -1.92 | 10.89 | >40 | Inactive | 7.98 | Active |
| 186 | 17504959 | 15.94 | 20.87 | 9.27 | 6.5 | >40 | Inactive | 8.05 | Active |
| 187 | 17513823 | 15.11 | 16.1 | -10.64 | -1.1 | >40 | Inactive | 8.08 | Active |
| 188 | 11532992 | 9.65 | 10.41 | 9.29 | 1.26 | >40 | Inactive | 8.1 | Active |
| 189 | 17513203 | 8.86 | 1.28 | 6.07 | 1.14 | >40 | Inactive | 8.16 | Active |
| 190 | 843534 | 12.86 | 5.53 | -2.2 | -0.78 | >40 | Inactive | 8.21 | Active |
| 191 | 14744504 | 11.74 | 3.25 | -4.39 | -0.63 | >40 | Inactive | 8.21 | Active |
| 192 | 14720713 | 10.29 | 17.07 | 3.89 | 2.67 | >40 | Inactive | 8.26 | Active |
| 193 | 17403000 | 8.68 | 5.69 | -0.17 | 1.73 | >40 | Inactive | 8.27 | Active |
| 194 | 17507647 | 0 | 0.32 | -7.35 | -5.2 | >40 | Inactive | 8.35 | Active |
| 195 | 17431981 | 8.52 | -2.11 | 3.38 | 0 | >40 | Inactive | 8.39 | Active |
| 196 | 17514263 | 17.68 | 7.48 | 2.53 | 4.24 | >40 | Inactive | 8.45 | Active |
| 197 | 17511660 | 18.68 | 11.24 | 6.55 | 11.38 | >40 | Inactive | 8.47 | Active |
| 198 | 17401399 | 11.59 | -0.96 | 6.23 | 2.11 | >40 | Inactive | 8.48 | Active |
| 199 | 17509685 | 27.17 | 19.84 | -5.57 | 1.73 | >40 | Inactive | 8.5 | Active |
| 200 | 14739910 | 58.84 | 23.41 | 61.15 | 50.39 | 7.18 | Active | 8.53 | Active |
| 201 | 17412454 | 4.35 | 0 | -1.92 | -8.29 | >40 | Inactive | 8.56 | Active |
| 202 | 7972504 | 4.83 | 6.74 | 3.35 | -0.33 | >40 | Inactive | 8.67 | Active |
| 203 | 22400390 | 9.02 | 5.14 | 4.15 | -5.53 | >40 | Inactive | 8.68 | Active |
| 204 | 17508838 | 10.79 | 10.43 | 3.67 | -5.69 | >40 | Inactive | 8.69 | Active |
| 205 | 17511723 | 4.98 | -2.6 | -3.72 | 6.12 | >40 | Inactive | 8.71 | Active |
| 206 | 17412290 | 7.4 | -1.46 | -8.11 | 0.63 | >40 | Inactive | 8.72 | Active |
| 207 | 17509437 | 14.49 | 11.4 | 1.44 | 4.39 | >40 | Inactive | 8.72 | Active |
| 208 | 17509538 | 15.3 | 7.54 | -3.19 | -5.04 | >40 | Inactive | 8.74 | Active |
| 209 | 4250306 | 12.24 | 3.21 | 4.15 | 10.41 | >40 | Inactive | 8.76 | Active |
| 210 | 17431648 | 10.13 | 0.98 | 1.69 | -6.28 | >40 | Inactive | 8.79 | Active |
| 211 | 14742704 | 3.54 | 1.77 | 4.47 | 1.95 | >40 | Inactive | 8.85 | Active |
| 212 | 7977397 | 14.95 | 13.5 | -3.89 | 6.91 | >40 | Inactive | 8.93 | Active |
| 213 | 853371 | 4.82 | 4.07 | -4.56 | 3.92 | >40 | Inactive | 8.94 | Active |
| 214 | 17410370 | 13.99 | 13.01 | -1.01 | -0.31 | >40 | Inactive | 8.96 | Active |
| 215 | 14737418 | 8.21 | 5.14 | 8.47 | -2.76 | >40 | Inactive | 8.97 | Active |
| 216 | 846045 | 11.9 | 1.63 | 8.78 | 1.88 | >40 | Inactive | 9.1 | Active |
| 217 | 22414029 | 17.55 | 10.11 | 0.96 | 3.58 | >40 | Inactive | 9.14 | Active |
| 218 | 22403389 | 11.58 | 12.03 | -2.2 | -3.61 | >40 | Inactive | 9.15 | Active |
| 219 | 22402006 | 17.85 | 9.11 | | 5.97 | >40 | Inactive | 9.17 | Active |
| 220 | 14729348 | 7.41 | 10.27 | -3.19 | -6.67 | >40 | Inactive | 9.18 | Active |
| 221 | 4241916 | 11.9 | 13.66 | -8.95 | 6.44 | >40 | Inactive | 9.26 | Active |
| 222 | 3712742 | 6.27 | -0.65 | 6.08 | 4.24 | >40 | Inactive | 9.27 | Active |
| 223 | 22402979 | 13.99 | 13.5 | 4.56 | 12.56 | >40 | Inactive | 9.27 | Active |
| 224 | 4259886 | 0.16 | -4.39 | -3.89 | -2.67 | >40 | Inactive | 9.27 | Active |
| 225 | 857019 | -2.57 | -0.98 | -3.89 | -1.88 | >40 | Inactive | 9.31 | Active |
| 226 | 856699 | 6.43 | 4.88 | -1.86 | -0.31 | >40 | Inactive | 9.33 | Active |
| 227 | 861942 | 4.66 | 1.79 | -6.08 | -5.18 | >40 | Inactive | 9.34 | Active |
| 228 | 17505774 | 7.4 | 14.8 | 3.21 | 3.77 | >40 | Inactive | 9.35 | Active |
| 229 | 22411589 | 8.04 | 1.46 | -2.36 | -0.63 | >40 | Inactive | 9.37 | Active |
| 230 | 17415101 | -4.51 | -3.37 | -5.27 | -1.95 | >40 | Inactive | 9.41 | Active |
| 231 | 17506458 | 11.58 | 9.59 | -3.38 | 0.31 | >40 | Inactive | 9.56 | Active |
| 232 | 22404244 | -4.03 | -1.77 | -13.1 | 0 | >40 | Inactive | 9.58 | Active |

Figure 16 (cont.)

| | | | | | | | | |
|---|---|---|---|---|---|---|---|---|
| 233 | 853404 | 5.95 | 3.58 | -10.47 | 1.1 | >40 | Inactive | 9.61 | Active |
| 234 | 17506495 | 16.24 | 15.61 | 4.22 | 10.36 | >40 | Inactive | 9.63 | Active |
| 235 | 14724580 | 18.65 | 3.41 | 9.8 | 4.87 | >40 | Inactive | 9.63 | Active |
| 236 | 14742754 | 4.66 | -5.69 | -3.72 | -0.94 | >40 | Inactive | 9.69 | Active |
| 237 | 22415067 | 2.25 | 5.78 | -1.12 | -3.58 | >40 | Inactive | 9.71 | Active |
| 238 | 863649 | 4.66 | 7.64 | -0.17 | 5.81 | >40 | Inactive | 9.72 | Active |
| 239 | 22407173 | 7.56 | 8.29 | 6.93 | 0.78 | >40 | Inactive | 9.75 | Active |
| 240 | 848716 | -3.06 | -6.9 | -9.11 | -8.46 | >40 | Inactive | 9.77 | Active |
| 241 | 14743151 | 10.45 | 6.18 | -16.05 | 0.63 | >40 | Inactive | 9.79 | Active |
| 242 | 22403961 | 7.41 | 9.31 | -2.88 | 3.58 | >40 | Inactive | 9.85 | Active |
| 243 | 17505915 | 11.76 | 9.31 | 0.96 | 1.63 | >40 | Inactive | 9.85 | Active |
| 244 | 3712694 | 10.61 | 1.3 | -13.01 | -3.61 | >40 | Inactive | 9.94 | Active |
| 245 | 7975442 | -2.42 | 4.49 | -8.31 | -5.2 | >40 | Inactive | 9.98 | Active |
| 246 | 861710 | -2.89 | 4.72 | -12.16 | -5.02 | >40 | Inactive | >10 | Inactive |
| 247 | 860274 | 10.45 | 8.94 | -7.26 | -4.87 | >40 | Inactive | >10 | Inactive |
| 248 | 858685 | 7.88 | -1.3 | -7.09 | 0.16 | >40 | Inactive | >10 | Inactive |
| 249 | 8139870 | -0.8 | -5.04 | 10.14 | 0.78 | >40 | Inactive | >10 | Inactive |
| 250 | 17414449 | -6.43 | -6.99 | -11.99 | -0.47 | >40 | Inactive | >10 | Inactive |
| 251 | 846382 | 0.48 | -9.27 | -5.24 | -5.81 | >40 | Inactive | >10 | Inactive |
| 252 | 22411961 | 2.09 | 0.16 | 2.7 | -0.47 | >40 | Inactive | >10 | Inactive |
| 253 | 14732069 | -1.61 | 0.98 | -1.01 | -2.2 | >40 | Inactive | >10 | Inactive |
| 254 | 7973376 | 0 | -3.25 | -2.03 | -7.54 | >40 | Inactive | >10 | Inactive |
| 255 | 859579 | 3.86 | -3.41 | -9.29 | 1.26 | >40 | Inactive | >10 | Inactive |
| 256 | 17408969 | 5.14 | 1.3 | -10.3 | 0.47 | >40 | Inactive | >10 | Inactive |
| 257 | 846821 | 4.5 | -12.03 | 0.17 | -3.61 | >40 | Inactive | >10 | Inactive |
| 258 | 17402799 | 0.64 | -6.67 | -3.89 | -6.59 | >40 | Inactive | >10 | Inactive |
| 259 | 22413959 | -2.25 | -11.38 | -9.12 | -3.14 | >40 | Inactive | >10 | Inactive |
| 260 | 22412503 | 6.43 | 7.32 | 3.21 | 3.14 | >40 | Inactive | >10 | Inactive |
| 261 | 22408718 | -7.56 | -10.57 | -11.66 | -7.54 | >40 | Inactive | >10 | Inactive |
| 262 | 14734044 | 0.32 | -11.87 | -9.29 | -6.59 | >40 | Inactive | >10 | Inactive |
| 263 | 847646 | 25.72 | 0 | -8.95 | -2.35 | >40 | Inactive | >10 | Inactive |
| 264 | 14737072 | -2.89 | -6.67 | -10.64 | -3.45 | >40 | Inactive | >10 | Inactive |
| 265 | 14745050 | -5.31 | -6.67 | -3.21 | -3.45 | >40 | Inactive | >10 | Inactive |
| 266 | 22411281 | 6.43 | 0.16 | -8.78 | 2.04 | >40 | Inactive | >10 | Inactive |
| 267 | 22407314 | 6.11 | -2.6 | -12.16 | 4.4 | >40 | Inactive | >10 | Inactive |
| 268 | 17507781 | 7.4 | 5.04 | -9.29 | 0 | >40 | Inactive | >10 | Inactive |
| 269 | 22415489 | 6.59 | -0.16 | -13.18 | -2.83 | >40 | Inactive | >10 | Inactive |
| 270 | 22413293 | 6.75 | 2.76 | -6.76 | -4.55 | >40 | Inactive | >10 | Inactive |
| 271 | 4244298 | 6.43 | 19.02 | -4.05 | -3.45 | >40 | Inactive | >10 | Inactive |
| 272 | 7969134 | 1.45 | -3.9 | 7.26 | -1.26 | >40 | Inactive | >10 | Inactive |
| 273 | 842942 | 3.38 | 2.28 | -0.34 | -0.78 | >40 | Inactive | >10 | Inactive |
| 274 | 14744380 | 4.02 | -3.74 | 0.84 | -0.47 | >40 | Inactive | >10 | Inactive |
| 275 | 17408627 | -4.18 | 10.73 | 1.35 | 10.83 | >40 | Inactive | >10 | Inactive |
| 276 | 858399 | 0 | -1.3 | -6.08 | 1.88 | >40 | Inactive | >10 | Inactive |
| 277 | 17507077 | 3.22 | -1.14 | -4.22 | 4.08 | >40 | Inactive | >10 | Inactive |
| 278 | 17407759 | 0.16 | 1.63 | -3.04 | 0.63 | >40 | Inactive | >10 | Inactive |
| 279 | 14741202 | -0.16 | 1.14 | -2.87 | 0.78 | >40 | Inactive | >10 | Inactive |
| 280 | 17514396 | 9.49 | 6.5 | 6.08 | 13.03 | >40 | Inactive | >10 | Inactive |
| 281 | 7977964 | -0.64 | 0.65 | -14.53 | 4.55 | >40 | Inactive | >10 | Inactive |
| 282 | 17513422 | 4.98 | 3.74 | -9.8 | -4.55 | >40 | Inactive | >10 | Inactive |
| 283 | 17507295 | 11.25 | 6.02 | -10.64 | -0.47 | >40 | Inactive | >10 | Inactive |
| 284 | 17413688 | 6.43 | 0 | -13.85 | 0.31 | >40 | Inactive | >10 | Inactive |
| 285 | 850880 | 0 | 0 | -4.22 | 6.28 | >40 | Inactive | >10 | Inactive |
| 286 | 7973241 | 3.7 | -2.44 | 0.68 | 2.98 | >40 | Inactive | >10 | Inactive |
| 287 | 17408238 | 0.16 | -2.28 | 0 | -1.57 | >40 | Inactive | >10 | Inactive |
| 288 | 22414831 | 2.41 | 13.5 | -0.51 | 4.71 | >40 | Inactive | >10 | Inactive |
| 289 | 14739181 | 1.13 | -0.16 | -4.05 | 3.61 | >40 | Inactive | >10 | Inactive |
| 290 | 17513686 | 8.2 | 0.49 | 2.53 | 7.38 | >40 | Inactive | >10 | Inactive |
| 291 | 17510724 | 12.22 | 1.79 | 8.61 | 0.78 | >40 | Inactive | >10 | Inactive |

Figure 16 (cont.)

| 292 | 14733687 | 1.93 | -2.6 | -4.73 | -1.26 | >40 | Inactive | >10 | Inactive |
|---|---|---|---|---|---|---|---|---|---|
| 293 | 22403882 | 8.36 | -1.63 | -3.21 | -3.92 | >40 | Inactive | >10 | Inactive |
| 294 | 4245780 | 5.63 | -3.58 | -11.82 | -4.08 | >40 | Inactive | >10 | Inactive |
| 295 | 22416150 | -0.64 | -0.16 | -6.93 | -1.26 | >40 | Inactive | >10 | Inactive |
| 296 | 4249272 | 2.41 | -3.41 | -0.84 | 1.88 | >40 | Inactive | >10 | Inactive |
| 297 | 17386024 | 3.7 | 4.72 | 0.34 | 1.41 | >40 | Inactive | >10 | Inactive |
| 298 | 17509581 | 3.05 | 0 | -3.72 | 2.83 | >40 | Inactive | >10 | Inactive |
| 299 | 17511420 | -0.48 | 0.49 | 3.89 | 4.71 | >40 | Inactive | >10 | Inactive |
| 300 | 14743148 | 18.49 | 15.93 | 1.86 | 7.06 | >40 | Inactive | >10 | Inactive |
| 301 | 17387142 | 9.32 | 2.6 | 4.05 | 2.2 | >40 | Inactive | >10 | Inactive |
| 302 | 852080 | 6.43 | -1.3 | -4.39 | -1.73 | >40 | Inactive | >10 | Inactive |
| 303 | 4263291 | 3.05 | 0.81 | 5.57 | 0 | >40 | Inactive | >10 | Inactive |
| 304 | 17431474 | 1.45 | 3.74 | -1.18 | -0.16 | >40 | Inactive | >10 | Inactive |
| 305 | 850527 | 0.8 | 6.99 | -6.08 | -7.06 | >40 | Inactive | >10 | Inactive |
| 306 | 17507822 | 8.2 | 3.25 | -10.81 | 5.02 | >40 | Inactive | >10 | Inactive |
| 307 | 17506750 | 6.43 | 0.65 | -8.95 | 7.06 | >40 | Inactive | >10 | Inactive |
| 308 | 14743902 | -1.13 | 7.8 | -10.14 | 8.48 | >40 | Inactive | >10 | Inactive |
| 309 | 17504960 | 5.31 | 5.37 | -1.69 | -0.63 | >40 | Inactive | >10 | Inactive |
| 310 | 14724549 | 0.16 | 0.49 | -2.2 | 4.24 | >40 | Inactive | >10 | Inactive |
| 311 | 17387000 | -8.2 | -11.06 | -14.7 | -9.89 | >40 | Inactive | >10 | Inactive |
| 312 | 22406960 | 3.86 | -6.83 | 4.56 | 3.61 | >40 | Inactive | >10 | Inactive |
| 313 | 14734948 | 0.96 | 1.95 | -4.39 | -3.14 | >40 | Inactive | >10 | Inactive |
| 314 | 14734500 | 11.9 | 4.23 | -3.72 | -0.16 | >40 | Inactive | >10 | Inactive |
| 315 | 4255843 | 7.07 | -3.25 | -3.72 | 6.12 | >40 | Inactive | >10 | Inactive |
| 316 | 22407496 | 10.13 | 8.94 | -0.84 | 10.05 | >40 | Inactive | >10 | Inactive |
| 317 | 17510132 | 2.25 | 3.09 | 0.84 | 1.1 | >40 | Inactive | >10 | Inactive |
| 318 | 14726339 | -4.18 | -0.49 | -11.99 | -1.1 | >40 | Inactive | >10 | Inactive |
| 319 | 22407574 | 2.09 | 2.11 | -6.93 | -3.61 | >40 | Inactive | >10 | Inactive |
| 320 | 17516881 | 0.8 | 6.02 | -10.81 | -6.44 | >40 | Inactive | >10 | Inactive |
| 321 | 24708177 | 19.61 | 11.71 | 8.95 | 7.38 | >40 | Inactive | >10 | Inactive |
| 322 | 7978181 | -0.8 | 0 | 6.25 | 5.81 | >40 | Inactive | >10 | Inactive |
| 323 | 17511817 | 13.34 | 6.67 | 15.54 | 8.16 | >40 | Inactive | >10 | Inactive |
| 324 | 14743067 | 12.54 | 2.28 | 9.12 | 1.88 | >40 | Inactive | >10 | Inactive |
| 325 | 4265410 | 2.25 | -2.6 | -1.35 | -3.3 | >40 | Inactive | >10 | Inactive |
| 326 | 7973301 | 9.16 | 4.72 | 6.25 | -4.71 | >40 | Inactive | >10 | Inactive |
| 327 | 17409574 | -2.89 | 9.59 | -5.57 | -1.88 | >40 | Inactive | >10 | Inactive |
| 328 | 17408048 | 5.95 | 2.28 | 9.8 | -1.41 | >40 | Inactive | >10 | Inactive |
| 329 | 4264126 | 2.41 | -2.6 | -4.9 | 1.57 | >40 | Inactive | >10 | Inactive |
| 330 | 14730831 | 8.04 | 9.11 | -1.01 | 0.47 | >40 | Inactive | >10 | Inactive |
| 331 | 4261215 | 12.54 | -4.39 | -6.93 | 0.16 | >40 | Inactive | >10 | Inactive |
| 332 | 17388092 | 14.95 | -2.11 | 0.68 | 9.58 | >40 | Inactive | >10 | Inactive |
| 333 | 22408547 | 5.14 | 3.74 | -1.52 | 7.38 | >40 | Inactive | >10 | Inactive |
| 334 | 4247073 | 11.74 | 8.13 | -2.36 | 7.38 | >40 | Inactive | >10 | Inactive |
| 335 | 17387409 | 0.48 | 2.28 | 3.21 | -1.57 | >40 | Inactive | >10 | Inactive |
| 336 | 17406953 | 5.31 | 2.76 | -10.47 | -0.16 | >40 | Inactive | >10 | Inactive |
| 337 | 22413437 | 8.36 | -2.11 | -9.63 | 1.88 | >40 | Inactive | >10 | Inactive |
| 338 | 14733736 | 2.57 | 12.2 | -9.29 | -2.51 | >40 | Inactive | >10 | Inactive |
| 339 | 4256294 | 4.82 | 3.41 | -2.2 | 5.02 | >40 | Inactive | >10 | Inactive |
| 340 | 22402963 | 2.57 | 5.2 | -8.28 | -0.94 | >40 | Inactive | >10 | Inactive |
| 341 | 4262116 | 4.82 | 1.79 | -3.89 | 3.61 | >40 | Inactive | >10 | Inactive |
| 342 | 843249 | 6.27 | 2.28 | 7.26 | -4.08 | >40 | Inactive | >10 | Inactive |
| 343 | 14744829 | -0.96 | 6.02 | 0.17 | 2.98 | >40 | Inactive | >10 | Inactive |
| 344 | 3713798 | 1.77 | 6.5 | 1.18 | 1.88 | >40 | Inactive | >10 | Inactive |
| 345 | 14742023 | 9 | 2.11 | 8.78 | -1.73 | >40 | Inactive | >10 | Inactive |
| 346 | 14735823 | 2.89 | 3.9 | 1.52 | -1.88 | >40 | Inactive | >10 | Inactive |
| 347 | 17411993 | 0.96 | 1.63 | -7.26 | -2.51 | >40 | Inactive | >10 | Inactive |
| 348 | 4258029 | 6.91 | 5.69 | -10.81 | -1.26 | >40 | Inactive | >10 | Inactive |
| 349 | 14733952 | 12.7 | 2.28 | -0.51 | 1.88 | >40 | Inactive | >10 | Inactive |
| 350 | 17503722 | -3.7 | -3.58 | -10.47 | 2.2 | >40 | Inactive | >10 | Inactive |

Figure 16 (cont.)

| 351 | 22413819 | -7.72 | 0.16 | -11.82 | -2.83 | >40 | Inactive | >10 | Inactive |
|---|---|---|---|---|---|---|---|---|---|
| 352 | 14743852 | -2.73 | -0.81 | -9.12 | -1.88 | >40 | Inactive | >10 | Inactive |
| 353 | 859256 | 10.61 | 12.2 | 6.59 | 6.91 | >40 | Inactive | >10 | Inactive |
| 354 | 17414164 | 12.7 | 7.32 | 11.82 | -1.41 | >40 | Inactive | >10 | Inactive |
| 355 | 14730356 | 7.07 | -5.37 | -2.7 | 4.4 | >40 | Inactive | >10 | Inactive |
| 356 | 16952415 | -1.13 | -9.43 | 1.01 | 0.78 | >40 | Inactive | >10 | Inactive |
| 357 | 17515487 | -0.64 | -4.07 | -4.22 | -1.73 | >40 | Inactive | >10 | Inactive |
| 358 | 3713467 | 6.11 | -0.81 | 2.2 | -2.35 | >40 | Inactive | >10 | Inactive |
| 359 | 17409037 | 2.89 | 3.58 | -0.51 | -0.78 | >40 | Inactive | >10 | Inactive |
| 360 | 7977250 | 6.11 | 4.72 | 1.18 | 3.77 | >40 | Inactive | >10 | Inactive |
| 361 | 17401190 | 4.5 | 2.6 | -2.2 | 3.14 | >40 | Inactive | >10 | Inactive |
| 362 | 7972274 | 0.32 | -2.44 | -1.69 | -3.3 | >40 | Inactive | >10 | Inactive |
| 363 | 17388004 | -5.31 | -5.85 | -2.2 | -3.14 | >40 | Inactive | >10 | Inactive |
| 364 | 17511303 | -2.57 | -5.04 | -8.45 | -0.47 | >40 | Inactive | >10 | Inactive |
| 365 | 17511759 | 8.2 | 8.62 | 4.56 | 4.71 | >40 | Inactive | >10 | Inactive |
| 366 | 7971201 | -4.34 | 0.16 | -4.39 | -2.83 | >40 | Inactive | >10 | Inactive |
| 367 | 17511772 | 1.13 | -5.04 | -4.56 | -0.94 | >40 | Inactive | >10 | Inactive |
| 368 | 17433710 | 4.82 | -0.16 | -3.04 | 6.44 | >40 | Inactive | >10 | Inactive |
| 369 | 861454 | 4.82 | 0.49 | 1.52 | 16.48 | >40 | Inactive | >10 | Inactive |
| 370 | 17433616 | 0.8 | 4.72 | 0.68 | 4.71 | >40 | Inactive | >10 | Inactive |
| 371 | 3712509 | 7.23 | 8.78 | 11.15 | 1.73 | >40 | Inactive | >10 | Inactive |
| 372 | 17433641 | 4.5 | 1.3 | 0.34 | 0.47 | >40 | Inactive | >10 | Inactive |
| 373 | 14734537 | 0 | -0.65 | 2.2 | -3.3 | >40 | Inactive | >10 | Inactive |
| 374 | 17507329 | 5.14 | -6.18 | -5.07 | 3.92 | >40 | Inactive | >10 | Inactive |
| 375 | 863762 | 6.11 | 5.37 | 13.01 | -7.85 | >40 | Inactive | >10 | Inactive |
| 376 | 17507123 | -1.77 | -1.3 | -7.6 | 4.71 | >40 | Inactive | >10 | Inactive |
| 377 | 22409577 | -1.61 | 2.93 | -2.36 | -0.16 | >40 | Inactive | >10 | Inactive |
| 378 | 17510229 | -3.7 | 6.18 | -6.25 | -1.1 | >40 | Inactive | >10 | Inactive |
| 379 | 17513971 | -3.7 | -2.11 | -20.78 | -8.01 | >40 | Inactive | >10 | Inactive |
| 380 | 846433 | -7.23 | -8.62 | -17.4 | -4.24 | >40 | Inactive | >10 | Inactive |
| 381 | 17514186 | -3.86 | -5.2 | -16.39 | -9.89 | >40 | Inactive | >10 | Inactive |
| 382 | 7972672 | -3.7 | -3.58 | -14.53 | -6.91 | >40 | Inactive | >10 | Inactive |
| 383 | 4243241 | -2.41 | -1.79 | -7.43 | -3.77 | >40 | Inactive | >10 | Inactive |
| 384 | 4254644 | -0.96 | -5.37 | -6.25 | -6.12 | >40 | Inactive | >10 | Inactive |
| 385 | 22406990 | 6.75 | 6.34 | -0.51 | -11.46 | >40 | Inactive | >10 | Inactive |
| 386 | 17385881 | 8.2 | 1.3 | 0.84 | -5.65 | >40 | Inactive | >10 | Inactive |
| 387 | 3712158 | -3.86 | -6.67 | -2.87 | -9.89 | >40 | Inactive | >10 | Inactive |
| 388 | 17413889 | -4.98 | -6.34 | -10.47 | -7.22 | >40 | Inactive | >10 | Inactive |
| 389 | 3711287 | -6.27 | -3.41 | -14.53 | -7.38 | >40 | Inactive | >10 | Inactive |
| 390 | 4258970 | -3.54 | -0.98 | -8.95 | -1.26 | >40 | Inactive | >10 | Inactive |
| 391 | 17415348 | -5.31 | 1.79 | -6.08 | -3.3 | >40 | Inactive | >10 | Inactive |
| 392 | 4250517 | 9.49 | 11.22 | 4.56 | 4.87 | >40 | Inactive | >10 | Inactive |
| 393 | 862679 | -0.8 | 7.32 | -3.04 | -3.45 | >40 | Inactive | >10 | Inactive |
| 394 | 7972089 | 9 | 3.58 | -7.09 | 0 | >40 | Inactive | >10 | Inactive |
| 395 | 7977322 | 2.57 | 0.98 | -5.74 | -3.92 | >40 | Inactive | >10 | Inactive |
| 396 | 14739389 | 16.72 | 5.2 | -4.39 | 0.94 | >40 | Inactive | >10 | Inactive |
| 397 | 17514219 | 11.58 | 6.99 | -0.17 | 9.58 | >40 | Inactive | >10 | Inactive |
| 398 | 14745321 | 13.5 | -2.28 | 3.55 | 5.34 | >40 | Inactive | >10 | Inactive |
| 399 | 865221 | 10.93 | 7.15 | 8.28 | 15.86 | >40 | Inactive | >10 | Inactive |
| 400 | 3716858 | 4.5 | -5.04 | -6.93 | -4.87 | >40 | Inactive | >10 | Inactive |
| 401 | 14724912 | 7.4 | -4.23 | 0.51 | -7.54 | >40 | Inactive | >10 | Inactive |
| 402 | 842469 | 10.61 | 3.25 | -7.77 | -3.61 | >40 | Inactive | >10 | Inactive |
| 403 | 7976604 | 9.81 | 4.07 | -7.77 | -4.87 | >40 | Inactive | >10 | Inactive |
| 404 | 3715904 | 9.32 | -2.44 | -2.87 | 2.2 | >40 | Inactive | >10 | Inactive |
| 405 | 847493 | 9 | 0.81 | -3.04 | -3.45 | >40 | Inactive | >10 | Inactive |
| 406 | 849497 | 13.04 | 14.93 | 0.8 | 3.25 | >40 | Inactive | >10 | Inactive |
| 407 | 22410214 | 12.08 | 7.38 | 4.15 | 10.73 | >40 | Inactive | >10 | Inactive |
| 408 | 845628 | -4.51 | 6.26 | -1.28 | 6.02 | >40 | Inactive | >10 | Inactive |
| 409 | 7969981 | 8.37 | 21.51 | 11.34 | 14.31 | >40 | Inactive | >10 | Inactive |

Figure 16 (cont.)

| 410 | 22411101 | 12.88 | 13 | 14.7 | 13.66 | >40 | Inactive | >10 | Inactive |
|---|---|---|---|---|---|---|---|---|---|
| 411 | 7972972 | 17.71 | 7.38 | 5.91 | 9.11 | >40 | Inactive | >10 | Inactive |
| 412 | 14735065 | 25.44 | 31.3 | 18.85 | 20 | <0.078 | Inconclusive | >10 | Inactive |
| 413 | 3717480 | 5.15 | 7.38 | 2.24 | 11.87 | >40 | Inactive | >10 | Inactive |
| 414 | 856752 | -2.58 | -3.21 | -9.11 | -1.95 | >40 | Inactive | >10 | Inactive |
| 415 | 14729216 | -10.47 | -12.84 | -13.26 | -11.87 | >40 | Inactive | >10 | Inactive |
| 416 | 22411630 | 6.12 | -1.93 | -3.51 | -7.97 | >40 | Inactive | >10 | Inactive |
| 417 | 17510010 | -3.86 | -2.73 | -10.54 | -11.54 | >40 | Inactive | >10 | Inactive |
| 418 | 852056 | 7.41 | -0.8 | -7.67 | -9.11 | >40 | Inactive | >10 | Inactive |
| 419 | 17402234 | -1.29 | -7.06 | -7.67 | -11.22 | >40 | Inactive | >10 | Inactive |
| 420 | 14741326 | 2.42 | 0.48 | 0.48 | -0.81 | >40 | Inactive | >10 | Inactive |
| 421 | 847052 | -2.42 | -5.46 | -10.06 | -9.11 | >40 | Inactive | >10 | Inactive |
| 422 | 14743272 | 7.09 | 2.89 | -2.08 | -0.81 | >40 | Inactive | >10 | Inactive |
| 423 | 4241575 | 3.86 | 2.09 | 0 | -9.76 | >40 | Inactive | >10 | Inactive |
| 424 | 4260201 | -0.16 | -0.48 | -7.67 | -5.53 | >40 | Inactive | >10 | Inactive |
| 425 | 14745419 | 1.93 | 6.58 | -7.51 | -2.93 | >40 | Inactive | >10 | Inactive |
| 426 | 17512730 | 12.4 | 13 | -3.19 | 4.72 | >40 | Inactive | >10 | Inactive |
| 427 | 853028 | 9.98 | -0.16 | -1.12 | -8.62 | >40 | Inactive | >10 | Inactive |
| 428 | 17408931 | 2.09 | 4.01 | -1.44 | -6.99 | >40 | Inactive | >10 | Inactive |
| 429 | 7974554 | 8.21 | -0.8 | -3.99 | -0.16 | >40 | Inactive | >10 | Inactive |
| 430 | 4248216 | -4.03 | 4.49 | 0 | -1.79 | >40 | Inactive | >10 | Inactive |
| 431 | 17508357 | 3.22 | 10.27 | -5.75 | -2.28 | >40 | Inactive | >10 | Inactive |
| 432 | 14723375 | -0.64 | 4.98 | 4.31 | 2.11 | >40 | Inactive | >10 | Inactive |
| 433 | 851438 | 3.38 | -1.77 | 0.64 | -0.81 | >40 | Inactive | >10 | Inactive |
| 434 | 17505154 | 12.56 | 1.12 | -5.59 | -2.6 | >40 | Inactive | >10 | Inactive |
| 435 | 17432356 | -1.45 | 4.65 | -0.64 | -2.11 | >40 | Inactive | >10 | Inactive |
| 436 | 4245588 | 12.24 | 9.47 | 4.95 | 4.88 | >40 | Inactive | >10 | Inactive |
| 437 | 17387602 | 1.29 | 7.7 | 1.6 | 6.18 | >40 | Inactive | >10 | Inactive |
| 438 | 17516375 | 6.12 | 2.57 | 0.64 | -0.16 | >40 | Inactive | >10 | Inactive |
| 439 | 4245341 | -0.32 | -0.64 | -8.31 | -2.6 | >40 | Inactive | >10 | Inactive |
| 440 | 14733989 | 4.03 | 2.57 | -2.72 | -4.07 | >40 | Inactive | >10 | Inactive |
| 441 | 4241115 | 7.89 | -3.21 | -1.12 | -2.44 | >40 | Inactive | >10 | Inactive |
| 442 | 17505388 | 8.37 | 1.12 | -5.75 | 0.81 | >40 | Inactive | >10 | Inactive |
| 443 | 17401202 | 7.57 | 4.65 | 1.92 | -3.25 | >40 | Inactive | >10 | Inactive |
| 444 | 851903 | 6.76 | 1.44 | -1.92 | 7.15 | >40 | Inactive | >10 | Inactive |
| 445 | 843090 | 23.83 | 2.25 | 6.87 | 0.33 | >40 | Inactive | >10 | Inactive |
| 446 | 14739249 | 3.22 | 8.99 | 2.72 | 15.28 | >40 | Inactive | >10 | Inactive |
| 447 | 849313 | 13.37 | -1.77 | 11.34 | 2.93 | >40 | Inactive | >10 | Inactive |
| 448 | 17514254 | 3.54 | 2.41 | -4.63 | 3.58 | >40 | Inactive | >10 | Inactive |
| 449 | 3713135 | 1.61 | 4.82 | 0 | -5.04 | >40 | Inactive | >10 | Inactive |
| 450 | 842596 | 10.14 | 4.01 | 8.95 | 6.5 | >40 | Inactive | >10 | Inactive |
| 451 | 4255938 | 0.16 | -1.28 | -7.83 | -5.53 | >40 | Inactive | >10 | Inactive |
| 452 | 22402738 | -2.25 | -0.32 | 1.6 | -1.79 | >40 | Inactive | >10 | Inactive |
| 453 | 4255688 | 15.14 | 14.61 | 13.58 | 8.46 | >40 | Inactive | >10 | Inactive |
| 454 | 17511574 | 17.87 | 3.05 | 18.69 | 7.48 | >40 | Inactive | >10 | Inactive |
| 455 | 17432189 | 8.37 | -6.42 | -1.92 | 0.49 | >40 | Inactive | >10 | Inactive |
| 456 | 14736259 | 5.15 | -1.28 | -2.4 | 2.28 | >40 | Inactive | >10 | Inactive |
| 457 | 14730727 | 4.19 | -1.77 | 5.59 | 7.15 | >40 | Inactive | >10 | Inactive |
| 458 | 22400576 | 4.35 | -1.44 | 0.64 | 1.3 | >40 | Inactive | >10 | Inactive |
| 459 | 847240 | 6.28 | -3.37 | -1.92 | 1.14 | >40 | Inactive | >10 | Inactive |
| 460 | 22401872 | 11.43 | 7.22 | 4.15 | 0.33 | >40 | Inactive | >10 | Inactive |
| 461 | 17413876 | 4.83 | -1.28 | 7.83 | 12.68 | >40 | Inactive | >10 | Inactive |
| 462 | 17408523 | 9.18 | 12.2 | -1.6 | -0.98 | 19.07 | Active | >10 | Inactive |
| 463 | 17506607 | 14.98 | 11.56 | 13.58 | 5.37 | >40 | Inactive | >10 | Inactive |
| 464 | 4265584 | -0.97 | 15.89 | -6.07 | 4.88 | >40 | Inactive | >10 | Inactive |
| 465 | 17403317 | 7.57 | 6.58 | 1.12 | -4.39 | >40 | Inactive | >10 | Inactive |
| 466 | 22405485 | 8.21 | -1.44 | -3.67 | -2.93 | >40 | Inactive | >10 | Inactive |
| 467 | 849099 | -0.16 | 2.09 | -3.51 | -4.39 | >40 | Inactive | >10 | Inactive |
| 468 | 14725349 | 2.25 | 19.42 | 1.12 | 3.25 | >40 | Inactive | >10 | Inactive |

Figure 16 (cont.)

| 469 | 859717 | -0.64 | 5.46 | -1.92 | -0.81 | >40 | Inactive | >10 | Inactive |
|---|---|---|---|---|---|---|---|---|---|
| 470 | 22405338 | 5.15 | -7.7 | -5.91 | -3.58 | >40 | Inactive | >10 | Inactive |
| 471 | 22403535 | -2.9 | -6.74 | -8.95 | -0.98 | >40 | Inactive | >10 | Inactive |
| 472 | 14728699 | 4.67 | 0.8 | -6.87 | -6.18 | >40 | Inactive | >10 | Inactive |
| 473 | 14729387 | -7.25 | -1.93 | 1.92 | -9.43 | >40 | Inactive | >10 | Inactive |
| 474 | 843046 | -3.54 | -1.12 | -4.31 | 2.76 | >40 | Inactive | >10 | Inactive |
| 475 | 861507 | 5.64 | -1.28 | -4.63 | -10.73 | >40 | Inactive | >10 | Inactive |
| 476 | 22414601 | 6.76 | 1.61 | 2.4 | -7.8 | >40 | Inactive | >10 | Inactive |
| 477 | 17406655 | 3.22 | 1.77 | -5.59 | -0.81 | >40 | Inactive | >10 | Inactive |
| 478 | 14746615 | 15.3 | 12.68 | -3.19 | 3.9 | >40 | Inactive | >10 | Inactive |
| 479 | 22404441 | 4.35 | 4.17 | -1.6 | 0.16 | >40 | Inactive | >10 | Inactive |
| 480 | 4248286 | -3.06 | -8.35 | -7.67 | -4.55 | >40 | Inactive | >10 | Inactive |
| 481 | 4259096 | 33.66 | 4.17 | 1.92 | -5.37 | >40 | Inactive | >10 | Inactive |
| 482 | 17511321 | 8.05 | 4.49 | 3.67 | -6.18 | >40 | Inactive | >10 | Inactive |
| 483 | 16953586 | 7.73 | 0.32 | -5.59 | 3.58 | >40 | Inactive | >10 | Inactive |
| 484 | 17410289 | 7.25 | 4.82 | 4.95 | 20 | >40 | Inactive | >10 | Inactive |
| 485 | 853147 | -8.53 | -5.46 | -8.15 | -13.33 | >40 | Inactive | >10 | Inactive |
| 486 | 14724659 | -8.86 | -5.46 | -10.22 | -10.41 | >40 | Inactive | >10 | Inactive |
| 487 | 7976292 | -10.79 | -3.37 | -11.34 | -10.89 | >40 | Inactive | >10 | Inactive |
| 488 | 7969315 | -4.67 | 3.05 | -11.82 | -3.9 | >40 | Inactive | >10 | Inactive |
| 489 | 14722726 | -7.89 | -4.49 | -13.74 | -6.5 | >40 | Inactive | >10 | Inactive |
| 490 | 17433768 | -9.18 | -6.58 | -11.34 | -5.85 | >40 | Inactive | >10 | Inactive |
| 491 | 14723116 | -1.77 | -2.89 | -14.22 | -5.37 | >40 | Inactive | >10 | Inactive |
| 492 | 852467 | -6.6 | 1.44 | -6.87 | -2.6 | >40 | Inactive | >10 | Inactive |
| 493 | 14743000 | -3.54 | 3.37 | -4.95 | -10.41 | >40 | Inactive | >10 | Inactive |
| 494 | 4249406 | -4.83 | -9.15 | -8.47 | -7.8 | >40 | Inactive | >10 | Inactive |
| 495 | 14736017 | -6.92 | -5.78 | -2.56 | -6.18 | >40 | Inactive | >10 | Inactive |
| 496 | 861069 | -7.89 | -9.31 | -7.03 | -0.33 | >40 | Inactive | >10 | Inactive |
| 497 | 14745740 | 17.07 | 4.82 | -5.43 | 5.53 | >40 | Inactive | >10 | Inactive |
| 498 | 16953763 | 2.74 | 5.14 | -0.48 | 1.63 | >40 | Inactive | >10 | Inactive |
| 499 | 865136 | 18.68 | 18.46 | 6.87 | 1.79 | >40 | Inactive | >10 | Inactive |

Figure 16 (cont.)

Table 2
| BKB/Goldfarb compound/company ID | PubChem SID | chemical name | fold improvement in DeaD lifespan in 0.75 mM NAM | | | structure |
|---|---|---|---|---|---|---|
| | | | 10 µM | 5 µM | 1 µM | |
| #3-11 (cluster 1 control) Asinex: BAS 00701525 | 14724551 | | 3.438 | 2.471 | 1.679 | 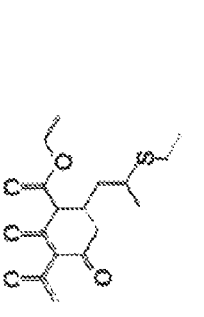 |
| S1-5 Chembridge: 5220056 | | 2-butyryl-5-[2-(ethylthio)propyl]-1,3-cyclohexanedione | 3.253 | 4.394 | 1.561 | 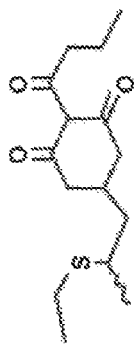 |
| S3-5 LABOTEST:LT00258229 | | | 3.027 | 3.755 | 3.043 | 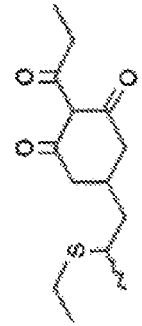 |
Figure 17

Table 2
| BKB/Goldfarb ID | compound/company ID | PubChem SID | chemical name | fold improvement in DeaD lifespan in 0.75 mM NAM | | | structure |
| --- | --- | --- | --- | --- | --- | --- | --- |
| | | | | 10 µM | 5 µM | 1 µM | |
| S3-9 | LABOTEST:LT02253383 | | | 3.091 | 3.311 | 1.992 | 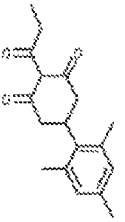 |
| S1-6 | Chembridge: 5220057 | | methyl 3-acetyl-6-[(2-(ethylthio)propyl]-2,4-dioxocyclohexanecarboxylate | 3.308 | 3.157 | 2.452 | 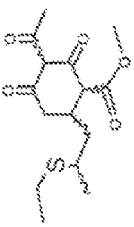 |
| S1-9 | Chembridge: 5220071 | | 5-phenyl-2-propionyl-1,3-cyclohexanedione | 1.712 | 2.615 | 2.500 | 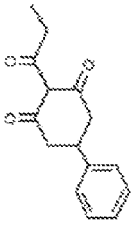 |
| S1-10 | Chembridge: 5220072 | | 2-pentanoyl-5-phenyl-1,3-cyclohexanedione | 2.208 | 2.590 | 1.628 | 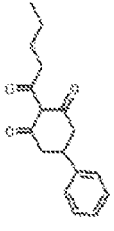 |
Figure 17 (cont.)

Table 2
| BKB/Goldfarb ID | compound/company ID | PubChem SID | chemical name | fold improvement in DeaD lifespan in 0.75 mM NAM | | | structure |
|---|---|---|---|---|---|---|---|
| | | | | 10 µM | 5 µM | 1 µM | |
| S2-3 | IBS: STOCK1N-06411 | | | 2.644 | 2.541 | 1.515 | 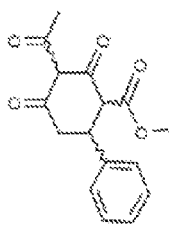 |
| S2-20 | Asinex: BAS 00701527 | | | 1.684 | 2.346 | 1.710 | 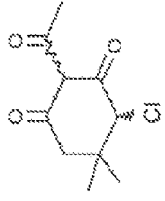 |
| S2-29 | LABOTEST: LT00257974 | | | 1.885 | 2.304 | 1.726 | 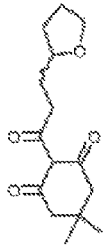 |
| S1-13 | Chembridge: 5220079 | | 5,5-dimethyl-2-(4-nitrobenzoyl)-1,3-cyclohexanedione | 2.327 | 2.301 | 1.151 | 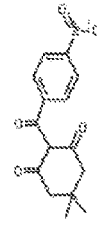 |
Figure 17 (cont.)

Table 2

| BKB/Goldfarb ID | compound/company ID | PubChem SID | chemical name | fold improvement in DeaD lifespan in 0.75 mM NAM | | | structure |
|---|---|---|---|---|---|---|---|
| | | | | 10 µM | 5 µM | 1 µM | |
| S2-6 | Pharmeks: PHAR153295/Ryan Scientific | | | 2.872 | 2.218 | 1.539 | |
| S1-11 | Chembridge: 5220075 | | methyl 2,4-dioxo-3-pentanoyl-6-phenylcyclohexanecarboxylate | 2.160 | 2.167 | 1.878 | 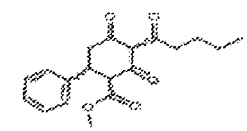 |
| S2-5 | IBS: STOCK1N-10732 | | | 1.056 | 2.020 | 1.185 | 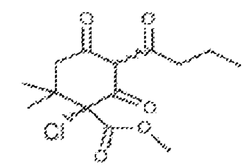 |
| S1-12 | Chembridge: 5220078 | | 5,5-dimethyl-2-(phenylacetyl)-1,3-cyclohexanedione | 2.837 | 2.003 | 1.375 | 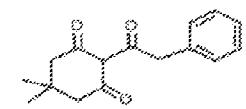 |

Figure 17 (cont.)

Table 2
| BKB/Goldfarb ID | compound/company ID | PubChem SID | chemical name | fold improvement in DeaD lifespan in 0.75 mM NAM | | | structure |
|---|---|---|---|---|---|---|---|
| | | | | 10 µM | 5 µM | 1 µM | |
| S2-31 | LABOTEST: LT00257600 | | | 1.372 | 1.654 | 1.151 | 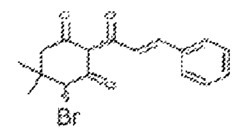 |
| S2-6 | IBS: STOCK1N-17230 | | | 1.584 | 1.630 | 1.314 | 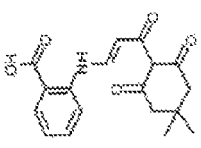 |
| S3-12 | LABOTEST: LT00298536 | | | 1.326 | 1.560 | 1.262 | 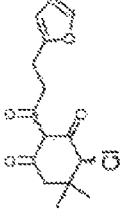 |
| S2-8 | Asinex: BAS 00703505 | | | 1.564 | 1.518 | 1.370 | 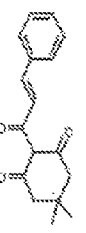 |
Figure 17 (cont.)

Table 2
| BKB/Goldfarb ID | compound/company ID | PubChem SID | chemical name | fold improvement in DeaD lifespan in 0.75 mM NAM | | | structure |
|---|---|---|---|---|---|---|---|
| | | | | 10 μM | 5 μM | 1 μM | |
| S2-14 | IBS: STOCK1S-58242 | | | 1.519 | 1.485 | 1.279 | 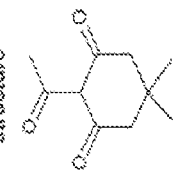 |
| S2-1 | Chembridge: 5320821 | | | 1.934 | 1.472 | 1.073 | 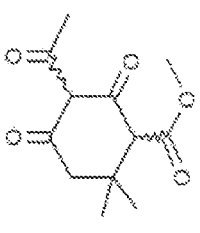 |
| S3-2 | Bionet: 4R-1127/Key Organics 4R-1127 | | | 1.240 | 1.432 | 0.857 | 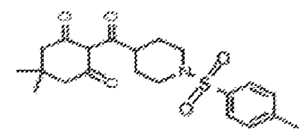 |
| S3-7 | LABOTEST-LIT02583?? | | | 1.402 | 1.420 | 1.204 | 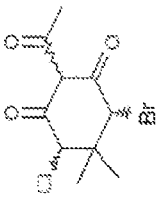 |
Figure 17 (cont.)

Table 2

| BKB/Goldfarb ID | compound/company ID | PubChem SID | chemical name | fold improvement in DeaD lifespan in 0.75 mM NAM | | | structures |
|---|---|---|---|---|---|---|---|
| | | | | 10 µM | 5 µM | 1 µM | |
| S1-8 | Chembridge: 5220070 | | 2-benzoyl-5,5-dimethyl-1,3-cyclohexanedione | 1.410 | 1.417 | 0.817 | 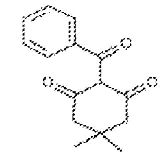 |
| S2-17 | IBS: STOCK2S-91393 | | | 0.834 | 1.375 | 0.719 | 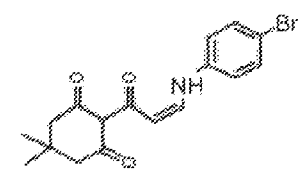 |
| S3-6 | LABOTEST:LT00259345 | | | 1.651 | 1.314 | 4.081 | |
| S3-4 | LABOTEST:LT00258301 | | | 1.368 | 1.304 | 1.189 | 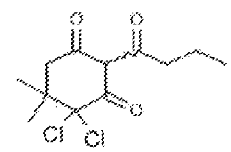 |

Table 2

| BKB/Goldfarb ID | compound/company ID | PubChem SID | chemical name | fold improvement in DeaD lifespan in 0.75 mM NAM | | | structure |
|---|---|---|---|---|---|---|---|
| | | | | 10 µM | 5 µM | 1 µM | |
| S3-1 | Bionet: 3R-1028/Key Organics 3R-1028 | | | 2.976 | 1.289 | 0.991 | 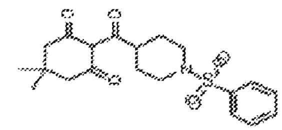 |
| S2-15 | IBS: STOCK1S-63471 | | | 0.955 | 1.272 | 0.995 | 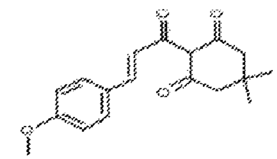 |
| S3-10 | LABOTEST:LT00258514 | | | 1.630 | 1.265 | 1.018 | 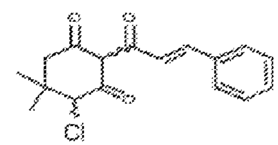 |
| S1-18 | Chembridge: 5320089 | | 2-butyryl-4-(3-methyl-5-isoxazolyl)-5-phenyl-1,3-cyclohexanedione | 1.410 | 1.256 | 1.083 | 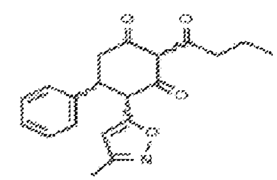 |

Table 2

| BKB/Goldfarb compound/company ID | PubChem SID | chemical name | fold improvement in DeaD lifespan in 0.75 mM NAM | | | structure |
|---|---|---|---|---|---|---|
| | | | 10 µM | 5 µM | 1 µM | |
| S1-7 | Chembridge: 5220062 | 2-benzoyl-4-chloro-5,5-dimethyl-1,3-cyclohexanedione | 1.359 | 1.208 | 1.513 | 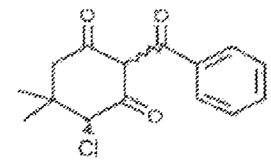 |
| S1-15 | Chembridge: 5220083 | -benzoyl-4,6-dichloro-5,5-dimethyl-1,3-cyclohexanedione | 0.913 | 1.183 | 1.256 | 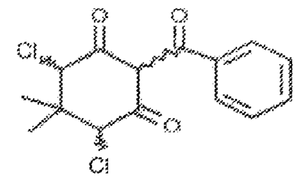 |
| S2-24 | LABOTEST-LT00258291 | | 1.318 | 1.176 | 1.068 | 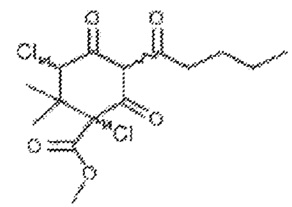 |
| S1-14 | Chembridge: 5220080 | methyl 2,2-dimethyl-5-(4-nitrobenzoyl)-4,6-dioxocyclohexanecarboxylate | 1.138 | 1.144 | 0.920 | 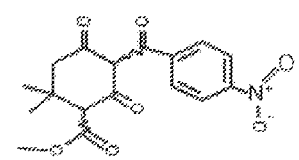 |

Figure 17 (cont.)

Table 2

| BKB/Goldfarb ID | compound/company ID | PubChem SID | chemical name | fold improvement in DeaD lifespan in 0.75 mM NAM | | | structure |
|---|---|---|---|---|---|---|---|
| | | | | 10 µM | 5 µM | 1 µM | |
| S2-13 | I85; STOCK1S-16103 | | | 0.643 | 1.106 | 1.172 | 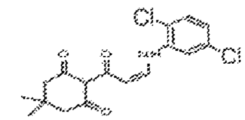 |
| S1-3 | Chembridge: 5220033 | | 2-[3-(3-furyl)acryloyl]-5,5-dimethyl-1,3-cyclohexanedione | 1.224 | 1.103 | 1.026 | 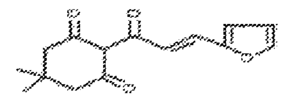 |
| S1-21 | Chembridge: 5690359 | | 4-[2-(4-methyl-2,6-dioxocyclohexyl)-2-oxoethyl]-2,6-piperidinedione | 0.994 | 1.061 | 1.045 | 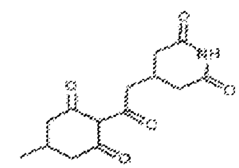 |
| S1-2 | Chembridge: 5220025 | | methyl 5-[3-(2-furyl)acryloyl]-2,2-dimethyl-4,6-dioxocyclohexanecarboxylate | 1.224 | 1.051 | 1.151 | 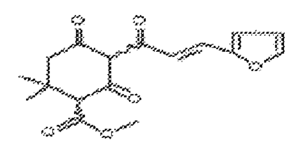 |

Figure 17 (cont.)

Table 2

| BKB/Goldfarb ID | compound/company ID | PubChem SID | chemical name | fold improvement in DeaD lifespan in 0.75 mM NAM | | | structure |
|---|---|---|---|---|---|---|---|
| | | | | 10 µM | 5 µM | 1 µM | |
| S1-1 | Chembridge: 5220022 | | methyl 5-butyryl-2,2-dimethyl-4,6-dioxocyclohexanecarboxylate | 1.404 | 1.038 | 1.388 | 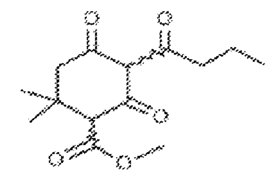 |
| S2-10 | IBS: STOCK1S-08678 | | | 1.105 | 1.021 | 1.176 | 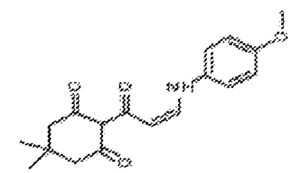 |
| S2-22 | LABOTEST-LT00257621 | | | 1.003 | 0.962 | 1.643 | 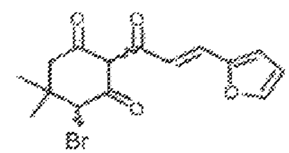 |
| S2-16 | IBS: STOCK1S-65450 | | | 1.371 | 0.915 | 1.104 | 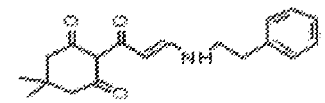 |

Table 2

| BKB/Goldfarb ID | compound/company ID | PubChem SID | chemical name | fold improvement in DeaD lifespan in 0.75 mM NAM | | | structure |
|---|---|---|---|---|---|---|---|
| | | | | 10 µM | 5 µM | 1 µM | |
| S1-22 | Chembridge: 5690964 | | 4-[2-(4,4-dimethyl-2,6-dioxocyclohexyl)-2-oxoethyl]-2,6-piperidinedione | 1.064 | 0.885 | 1.057 | 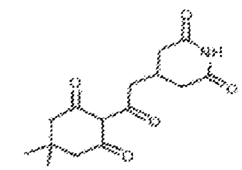 |
| S2-11 | IBS: STOCK1S-09853 | | | 1.002 | 0.869 | 0.879 | 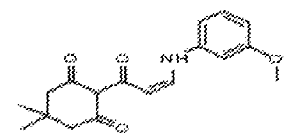 |
| S2-18 | IBS: STOCK3S-25676 | | | 1.057 | 0.863 | 1.061 | 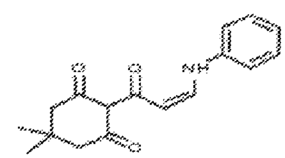 |
| S2-9 | IBS: STOCK1S-00487 | | | 1.224 | 0.713 | 0.921 | 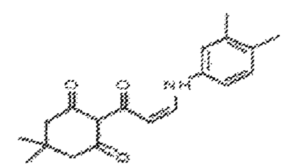 |

Table 2

| BKB/Goldfarb ID | compound/company ID | PubChem SID | chemical name | fold improvement in DeaD lifespan in 0.75 mM NAM | | | structure |
|---|---|---|---|---|---|---|---|
| | | | | 10 µM | 5 µM | 1 µM | |
| S1-20 | Chembridge: 5229530 | | methyl 5-cinnamoyl-2,2-dimethyl-4,6-dioxocyclohexanecarboxylate | 0.696 | 0.667 | 0.856 | 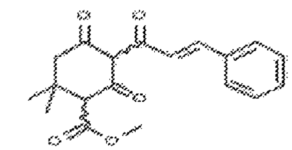 |
| S2-2 | IBS: STOCK1R-03212 | | | NOT TESTED: not soluble in DMSO, even at 5 mM | NOT TESTED: not soluble in DMSO, even at 5 mM | NOT TESTED: not soluble in DMSO, even at 5 mM | 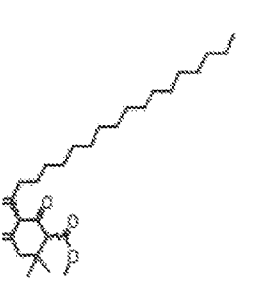 |
| S2-4 | IBS: STOCK1N-19652 | | | NOT TESTED: not soluble in DMSO, even at 5 mM | NOT TESTED: not soluble in DMSO, even at 5 mM | NOT TESTED: not soluble in DMSO, even at 5 mM | 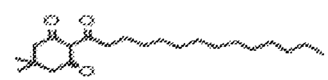 |
| S3-3 | Sigma Aldrich R614039 | | | NOT TESTED: not soluble in DMSO, even at 5 mM | NOT TESTED: not soluble in DMSO, even at 5 mM | NOT TESTED: not soluble in DMSO, even at 5 mM | 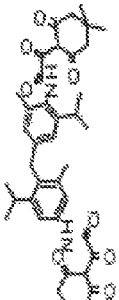 |

Figure 17 (cont.)

Table 4

| | 5 mM nic alone (12.1) | 1 µM S1-6 (16.1) | 2.5 µM S1-6 | 5 µM S1-6 | 0.5 µM S1-9 | 1 µM S1-9 (14.8) | 2.5 µM S1-9 |
|---|---|---|---|---|---|---|---|
| 1 | | 20 | 13 | 15 | 12 | 12 | 13 |
| 2 | 15 | 13 | 18 | 16 | 17 | 22 | |
| 3 | | 12 | 16 | 12 | 13 | 11 | 11 |
| 4 | 17 | 14 | 17 | 18 | 12 | 16 | 20 |
| 5 | 9 | 17 | 10 | 18 | 9 | 19 | 15 |
| 6 | 15 | 17 | 10 | 16 | 9 | 11 | 12 |
| 7 | 12 | 16 | | 18 | 15 | 11 | 16 |
| 8 | 10 | 20 | 13 | 11 | 16 | | |
| 9 | 6 | | 16 | 17 | 15 | 13 | 18 |
| 10 | 14 | 13 | 15 | 8 | 13 | 11 | 17 |
| 11 | 13 | 17 | 11 | | 2 | 14 | 14 |
| 12 | 18 | 11 | 22 | 15 | | 14 | 15 |
| 13 | 10 | 21 | 17 | 14 | 14 | 19 | 10 |
| 14 | 9 | 18 | | 9 | 19 | 13 | 14 |
| 15 | | 14 | 23 | 13 | | 14 | 13 |
| 16 | | 17 | 17 | | | 18 | 2 |
| 17 | 12 | 19 | 21 | 11 | 10 | 14 | 17 |
| 18 | | 14 | 9 | 15 | 24 | | |
| 19 | 12 | 16 | 18 | 12 | 13 | 15 | 17 |
| 20 | 9 | 16 | 13 | | 18 | 19 | 13 |
| | 5 mM nic alone (12.1) | 1 µM S1-6 (16.1) | 2.5 µM S1-6 | 5 µM S1-6 | 0.5 µM S1-9 | 1 µM S1-9 (14.8) | 2.5 µM S1-9 |
| count | 15 | 19 | 18 | 17 | 17 | 18 | 17 |
| average | 12.1 | 16.1 | 15.5 | 14.0 | 13.6 | 14.8 | 13.9 |
| max | 18 | 21 | 23 | 18 | 24 | 22 | 20 |

Figure 18

Table 4

| | SID | Common Name | IUPAC Name |
|---|---|---|---|
| 1 | 4251887 | 4-fluoro-N-[5-(2-furyl)-1,3,4-oxadiazol-2-yl]-1,3-benzothiazol-2-amine | 4-fluoro-N-(5-furan-2-yl-1,3,4-oxadiazol-2-yl)-1,3-benzothiazol-2-amine |
| 2 | 4245630 | 2-(3-chlorophenyl)-3-hydroxyquinazolin-4(3H)-one | 2-(3-chlorophenyl)-3-hydroxyquinazolin-4-one |
| 3 | 16953124 | 2-Hydroxy-benzoic acid [1-(1,3-dioxo-indan-2-yl)-ethylidene]-hydrazide | N-[1-(1,3-dioxoinden-2-yl)ethylideneamino]-2-hydroxybenzamide |
| 4 | 17402577 | 6-ethyl-4-hydroxy-2H-pyrano[3,2-c]quinoline-2,5(6H)-dione | 6-ethyl-2-hydroxypyrano[3,2-c]quinoline-4,5-dione |
| 5 | 17402574 | 4-hydroxy-6-isopropyl-2H-pyrano[3,2-c]quinoline-2,5(6H)-dione | 2-hydroxy-6-propan-2-ylpyrano[3,2-c]quinoline-4,5-dione |
| 6 | 22400413 | 4-Hydroxy-2-oxo-1,2-dihydro-quinoline-3-carboxylic acid [1-phenyl-meth-(E)-ylidene]-hydrazide | 2-hydroxy-4-oxo-N-(phenylmethylideneamino)-1H-quinoline-3-carboxamide |
| 7 | 857671 | | 1-(4-fluorophenyl)-3-morpholin-4-yl-2-phenylpropan-1-one hydrochloride |
| 8 | 17512647 | 3-Nitro-1-{[(E)-pyridin-4-ylmethylimino]-methyl}-6,7,8,9-tetrahydro-dibenzofuran-2-ol | (1Z)-3-nitro-1-[(pyridin-4-ylmethylamino)methylidene]-6,7,8,9-tetrahydrodibenzofuran-2-one |
| 9 | 17507366 | 1-(2,4-Dichloro-phenyl)-3-phenyl-2-[1,2,4]triazol-1-yl-propenone | (Z)-1-(2,4-dichlorophenyl)-3-phenyl-2-(1,2,4-triazol-1-yl)prop-2-en-1-one |
| 10 | 4245922 | 5-tert-butyl-4,5,6,7-tetrahydro-1H-indazole-3-carboxylic acid | 5-tert-butyl-4,5,6,7-tetrahydro-1H-indazole-3-carboxylic acid |
| 11 | 4263828 | ethyl 3-{[4-phenyl-6-(trifluoromethyl)-2-pyrimidinyl]sulfonyl}propanoate | ethyl 3-[4-phenyl-6-(trifluoromethyl)pyrimidin-2-yl]sulfonyl]propanoate |
| 12 | 862076 | | 2-cyclohexylsulfanyl-3-methoxyquinazolin-4-one |

Figure 19

| | | | |
|---|---|---|---|
| 13 | 4250971 | 3-hydroxy-2-quinoxalin-2-yl-2,3-dihydroquinazolin-4(1H)-one | -hydroxy-2-quinoxalin-2-yl-1,2-dihydroquinazolin-4-one |
| 14 | 7978235 | | 2-[[3-(5-bromopyridin-2-yl)-4-oxoquinazolin-2-yl]methyl]isoindole-1,3-dione |
| 15 | 7965978 | see Compound 15 structure | |
| 16 | 22413972 | 7-chloro-1,3,6-trimethyl-2,4(1H,3H)-pteridinedione | 7-chloro-1,3,6-trimethylpteridine-2,4-dione |
| 17 | 847157 | 2-(3-Oxo-1,3-dihydro-indol-2-ylidene)-indan-1,3-dione | 2-(3-oxo-1H-indol-2-ylidene)indene-1,3-dione |
| 18 | 17510022 | ethyl {2-[(Z)-2-nitrovinyl]phenoxy}acetate | ethyl 2-[2-[(Z)-2-nitroethenyl]phenoxy]acetate |
| 19 | 14734026 | 7-(2-furylmethyl)-N-[3-(1H-imidazol-1-yl)propyl]-5,6-diphenyl-7H-pyrrolo[2,3-d]pyrimidin-4-amine | 7-(furan-2-ylmethyl)-N-(3-imidazol-1-ylpropyl)-5,6-di(phenyl)pyrrolo[3,2-e]pyrimidin-4-amine |
| 20 | 14743053 | 3-(4-Phenyl-6-trifluoromethyl-pyrimidine-2-sulfonyl)-propionic acid methyl ester | methyl 3-[4-phenyl-6-(trifluoromethyl)pyrimidin-2-yl]sulfonylpropanoate |
| 21 | 14724551 | 3-Acetyl-6-(2-ethylsulfanyl-propyl)-2,4-dioxo-cyclohexanecarboxylic acid ethyl ester | ethyl 3-acetyl-6-(2-ethylsulfanylpropyl)-2,4-dioxocyclohexane-1-carboxylate |
| 22 | 17505716 | 2-hydroxy-6-methoxy-1H-benzo[de]isoquinoline-1,3(2H)-dione | |
| 23 | 17415346 | methyl 3-(1-methyl-1H-indol-3-yl)-2-nitroacrylate | methyl (Z)-3-(1-methylindol-3-yl)-2-nitroprop-2-enoate |
| 24 | 22401805 | 4-Hydroxy-2-oxo-1,2-dihydro-quinoline-3-carboxylic acid [1-(4-fluoro-phenyl)-meth-(E)-ylidene]-hydrazide | N-[(4-fluorophenyl)methylideneamino]-2-hydroxy-4-oxo-1H-quinoline-3-carboxamide |
| 25 | 14732512 | 2-butyryl-5-[2-(ethylthio)propyl]-1,3-cyclohexanedione | 2-butanoyl-5-(2-ethylsulfanylpropyl)cyclohexane-1,3-dione |
| 26 | 17512049 | 1-[(E)-Benzylimino-methyl]-3-nitro-6,7,8,9-tetrahydro-dibenzofuran-2-ol | (1Z)-3-nitro-1-[(phenylmethylamino)methylidene]-6,7,8,9-tetrahydrodibenzofuran-2-one |
| 27 | 14733039 | 2-[2-(4-chlorophenyl)hydrazono]-3-oxo-3-(4-pyridinyl)propanal | 2-[(4-chlorophenyl)hydrazinylidene]-3-oxo-3-pyridin-4-ylpropanal |

Figure 19 (cont.)

| | | | |
|---|---|---|---|
| 28 | 14730554 | (Z)-4-(4-Chloro-phenyl)-2-hydroxy-4-oxo-but-2-enoic acid N'-(2-hydroxy-2,2-diphenyl-acetyl)-hydrazide | (Z)-4-(4-chlorophenyl)-4-hydroxy-N'-[2-hydroxy-2,2-di(phenyl)acetyl]-2-oxobut-3-enehydrazide |
| 29 | 17402008 | | 2-hydroxy-N'-[(1Z)-1-(6-methyl-2,4-dioxopyran-3-ylidene)ethyl]benzohydrazide |
| 30 | 22412422 | 7,7-dimethyl-13-oxo-7,8,8a,13-tetrahydrobenzo[h]isoindolo[2,1-a]quinoline-12-carboxylicacid | |
| 31 | 17411197 | 5,5-dimethyl-3-oxo-1-cyclohexenyl 4-methylbenzenecarboxylate | (5,5-dimethyl-3-oxo-1-cyclohexenyl) 4-methylbenzoate |
| 32 | 17511154 | 2-(4-bromophenyl)-3-[(4-methoxybenzoyl)oxy]quinazolin-4(3H)-one | [2-(4-bromophenyl)-4-oxoquinazolin-3-yl] 4-methoxybenzoate |
| 33 | 17506345 | 4-(4-chlorophenyl)-N-(1,5-dimethyl-3-oxo-2-phenyl-2,3-dihydro-1H-pyrazol-4-yl)-2-hydroxy-4-oxo-2-butenamide | (E)-4-(4-chlorophenyl)-N-(1,5-dimethyl-3-oxo-2-phenylpyrazol-4-yl)-4-hydroxy-2-oxobut-3-enamide |
| 34 | 4249431 | 4-fluoro-N-(5-phenyl-1,3,4-oxadiazol-2-yl)-1,3-benzothiazol-2-amine | 4-fluoro-N-(5-phenyl-1,3,4-oxadiazol-2-yl)-1,3-benzothiazol-2-amine |
| 35 | 3717077 | | 3-[2-(2-methyl-2,3-dihydroindol-1-yl)-2-oxoethyl]quinazolin-4-one |
| 36 | 17507466 | 4-Ethyl-2,6-bis-pyridin-3-ylmethylene-cyclohexanone | (2E,6E)-4-ethyl-2,6-bis(pyridin-3-ylmethylidene)cyclohexan-1-one |
| 37 | 3712052 | | 4-(4-fluorophenyl)-2-(furan-2-carbonylamino)thiophene-3-carboxylic acid |
| 38 | 17508428 | 3-(1-Methyl-1H-indol-3-yl)-2-nitro-acrylic acid ethyl ester | ethyl (E)-3-(1-methylindol-3-yl)-2-nitroprop-2-enoate |
| 39 | 22413395 | 2-[1-(2-methoxyanilino)butylidene]-5-phenyl-1,3-cyclohexanedione | 2-[1-[(2-methoxyphenyl)amino]butylidene]-5-phenylcyclohexane-1,3-dione |
| 40 | 22402211 | 4-Hydroxy-2-oxo-1,2-dihydro-quinoline-3-carboxylic acid [1-(3-fluoro-phenyl)-meth-(E)-ylidene]-hydrazide | N-[(3-fluorophenyl)methylideneamino]-2-hydroxy-4-oxo-1H-quinoline-3-carboxamide |

Figure 19 (cont.)

| | | |
|---|---|---|
| 41 | 842207 | 1-Butyl-4-hydroxy-2-oxo-1,2-dihydro-quinoline-3-carboxylic acid pyrazin-2-ylamide / 1-butyl-2-hydroxy-4-oxo-N-pyrazin-2-ylquinoline-3-carboxamide |
| 42 | 17514347 | [6-[(4,6-dimethylpyrimidin-2-yl)sulfanylmethyl]-4-oxopyran-3-yl] 5-bromofuran-2-carboxylate |
| 43 | 17510012 | N-(4-ethoxyphenyl)-N-{[1-(2-phenoxyethyl)-1H-benzoimidazol-2-yl]methyl}amine / 4-ethoxy-N-[[1-[2-(phenoxy)ethyl]benzimidazol-2-yl]methyl]aniline |
| 44 | 17510032 | (6Z)-5-imino-3-(methylthio)-6-(thien-2-ylmethylene)-5,6-dihydro-7H-[1,2,4]thiadiazolo[4,5-a]pyrimidin-7-one / (6Z)-5-imino-3-methylsulfanyl-6-(thiophen-2-ylmethylidene)-[1,2,4]thiadiazolo[4,5-a]pyrimidin-7-one |
| 45 | 4241889 | 2-(methylsulfonyl)-4-phenyl-6-(trifluoromethyl)pyrimidine / 2-methylsulfonyl-4-phenyl-6-(trifluoromethyl)pyrimidine |
| 46 | 17511396 | N-(2-{[(E)-1-Ethyl-1H-benzoimidazol-2-ylimino]-methyl}-phenyl)-4-methyl-benzenesulfonamide / N-[2-[(1-ethylbenzimidazol-2-yl)iminomethyl]phenyl]-4-methylbenzenesulfonamide |
| 47 | 4243054 | 3-[(4-ethoxyphenoxy)acetyl]-4-hydroxy-2H-chromen-2-one / 3-[2-(4-ethoxyphenoxy)acetyl]-2-hydroxychromen-4-one |
| 48 | 14731075 | (Z)-4,4-Dimethyl-1-(3-nitro-phenyl)-2-[1,2,4]triazol-1-yl-pent-1-en-3-one / (Z)-4,4-dimethyl-1-(3-nitrophenyl)-2-(1,2,4-triazol-1-yl)pent-1-en-3-one |
| 49 | 14737835 | 2-(4-methylbenzoyl)indene-1,3-dione |
| 50 | 17511815 | N-(2-{[(E)-1-Butyl-1H-benzoimidazol-2-ylimino]-methyl}-phenyl)-4-methyl-benzenesulfonamide / N-[2-[(1-butylbenzimidazol-2-yl)iminomethyl]phenyl]-4-methylbenzenesulfonamide |
| 51 | 17513297 | 1,3-Diethyl-5-(5-methyl-thiophen-2-ylmethylene)-2-thioxo dihydro-pyrimidine-4,6-dione / 1,3-diethyl-5-[(5-methylthiophen-2-yl)methylidene]-2-sulfanylidene-1,3-diazinane-4,6-dione |
| 52 | 855620 | 1-ethyl-7-methyl-4-oxo-1,8-naphthyridine-3-carboxylic acid |
| 53 | 222414503 | (4-{[(2-hydroxy-1-naphthyl)methylene]amino}phenyl)acetic acid / 2-[4-[[(Z)-(2-oxonaphthalen-1-ylidene)methyl]amino]phenyl]acetic acid |
| 54 | 4251594 | 2-(methylsulfonyl)-4-thien-2-yl-6-(trifluoromethyl)pyrimidine / 2-methylsulfonyl-4-thiophen-2-yl-6-(trifluoromethyl)pyrimidine |

Figure 19 (cont.)

| # | ID | Name (col 1) | Name (col 2) |
|---|---|---|---|
| 55 | 17504927 | 4-{[5-(2-nitrophenyl)-2-furyl]methylene}-3-phenyl-5(4H)-isoxazolone | (4Z)-4-[[5-(2-nitrophenyl)furan-2-yl]methylidene]-3-phenyl-1,2-oxazol-5-one |
| 56 | 22414623 | N-(2,2,2-trichloro-N-isobutylethanimidoyl)benzenesulfonamide | 2,2,2-trichloro-N'-(2-methylpropyl)-N-phenylsulfonylethanimidamide |
| 57 | 17410531 | 2-(methylsulfanyl)-5,6,7,8-tetrahydro-4-quinazolinyl 4-chlorobenzenecarboxylate | (2-methylsulfanyl-5,6,7,8-tetrahydroquinazolin-4-yl) 4-chlorobenzoate |
| 58 | 17410710 | 2-chloro-1-(5-{[3-chloro-5-(trifluoromethyl)-2-pyridinyl]methyl}-2-thienyl)-1-ethanone | 2-chloro-1-[5-[[3-chloro-5-(trifluoromethyl)pyridin-2-yl]methyl]thiophen-2-yl]ethanone |
| 59 | 4243100 | 4-(2-furyl)-2-(methylsulfonyl)-6-(trifluoromethyl)pyrimidine | 4-furan-2-yl-2-methylsulfonyl-6-(trifluoromethyl)pyrimidine |
| 60 | 17511447 | 4-Methyl-N-{2-[(E)-o-tolylimino-methyl]-phenyl}-benzenesulfonamide | 4-methyl-N-[2-[(2-methylphenyl)iminomethyl]phenyl]benzenesulfonamide |
| 61 | 7967942 | | 2-cyclohexyl-3-oxo-1H-isoindole-4-carboxylic acid |
| 62 | 22413469 | 2-[1-(2-methoxyanilino)pentylidene]-5-phenyl-1,3-cyclohexanedione | 2-[1-[(2-methoxyphenyl)amino]pentylidene]-5-phenylcyclohexane-1,3-dione |
| 63 | 17402120 | 4-[(3-chlorophenyl)sulfanyl]-2-(2-pyridinyl)-5-pyrimidinyl methyl ether | 4-(3-chlorophenyl)sulfanyl-5-methoxy-2-pyridin-2-ylpyrimidine |
| 64 | 17433901 | 4-methyl-2,6-bis(3-pyridinylmethylene)cyclohexanone | (2E,6E)-4-methyl-2,6-bis(pyridin-3-ylmethylidene)cyclohexan-1-one |
| 65 | 22411681 | 4-hydroxy-5-methyl-1,6-diphenyl-3-(phenylsulfinyl)-2(1H)pyridinone | 2-hydroxy-5-methyl-1,6-di(phenyl)-3-phenylsulfinylpyridin-4-one |
| 66 | 17511642 | 5,5-Dimethyl-2-[2-(2-nitro-phenyl)-acetyl]-cyclohexane-1,3-dione | 5,5-dimethyl-2-[2-(2-nitrophenyl)acetyl]cyclohexane-1,3-dione |

Figure 19 (cont.)

| # | ID | Name |
|---|---|---|
| 67 | 847599 | 1-Hydroxy-3-oxo-6,7-dihydro-3H,5H-pyrido[3,2,1-ij]quinoline-2-carboxylic acid (5-isopropyl-[1,3,4]thiadiazol-2-yl)-amide |
| 68 | 844675 | 6-Hydroxy-4-oxo-1,2-dihydro-4H-pyrrolo[3,2,1-ij]quinoline-5-carboxylic acid pyridin-3-ylamide |
| 69 | 16953263 | 4-amino-2-[3-(3,5-dimethylpiperidin-1-yl)sulfonylbenzoyl]isoindole-1,3-dione |
| 70 | 846246 | 1-(3-Fluoro-4-methoxy-phenyl)-3-morpholin-4-yl-2-phenyl-propan-1-one |
| 71 | 17432193 | ethyl 1-hexyl-4,5-dioxo-3-pyrrolidinecarboxylate |
| 72 | 17433800 | dimethyl 7-(5-bromo-2-hydroxyphenyl)-2-oxo-3,7-dihydro 2H-thiopyrano[2,3-d][1,3]thiazole-5,6-dicarboxylate |
| 73 | 17513719 | 3-Methyl-2,4-dimethylene-1,5-diphenyl-pentane-1,5-dione |
| 74 | 22407084 | [4-[(E)-2-(2-methoxyethoxycarbonyl)-3-oxobut-1-enyl]phenyl] benzoate |
| 75 | 22407124 | [4-[(E)-2-ethoxycarbonyl-3-oxobut-1-enyl]phenyl] benzoate |
| 76 | 17432366 | N-(1,5-dimethyl-3-oxo-2-phenyl-2,3-dihydro-1H-pyrazol-4-yl)-2-hydroxy-4-oxo-4-phenyl-2-butenamide |
| 77 | 22402128 | [(7-chloro-4-oxochromen-3-yl)methylideneamino]thiourea |

Figure 19 (cont.)

METHOD FOR ALTERING THE LIFESPAN OF EUKARYOTIC ORGANISMS

CROSS-REFERENCE TO RELATED APPLICATIONS

This application claims priority to U.S. provisional patent application nos. 61/016,362, filed Dec. 21, 2007, and 61/023,801, filed Jan. 25, 2008, the disclosures of which are each incorporated herein by reference.

FEDERAL FUNDING

The work described herein was funded, in whole or in part, by grants from the National Institutes of Health (Grant Nos. MH076395 and NS0507987). Consequently, the federal government has certain rights in this invention.

FIELD OF USE

The present invention relates to methods for altering lifespan. Specifically, the invention relates to methods of increasing the lifespan of eukaryotic organisms.

BACKGROUND OF THE INVENTION

Many studies have confirmed that caloric restriction (CR) (synonymously, dietary restriction) extends lifespan in a range of non-human organisms including budding yeast (*Saccharomyces cerevisiae*), worms (*Caenorhabditis elegans*), the fruit fly (*Drosophila melanogaster*), and the mouse (*Mus musculus*). Based on the broad conservation of CR in animals, it is likely that a similar mechanism or mechanisms for CR-based lifespan extension also operates in humans. This intriguing observation opens the way to the possible extension of human lifespan by oral medications or other interventions, as opposed to (or as a supplement to) changes in diet, socioeconomic status, access to healthcare, etc.

In addition to the effects of CR on lifespan, other studies suggest that CR is likely to delay the onset or reduce the incidence of age-related diseases in humans, including cancer, diabetes, and cardiovascular disease, thus offering up a second critical reason to study the mechanism(s) of action of CR. Thus, for example resveratrol, a plant product that is a component of red wine, has been shown to have positive effects on the health and survival of "middle-aged" or overweight mice in ways that may correlate with protective methods for, e.g., diabetes (see, e.g., Baur et al., Nature (2006) 444:337-342), and has also been shown to provide protection against metabolic disease (see, e.g., Lagouge et al., Cell (2006) 127:1109-1122). In both cases, the action of resveratrol is thought to be mediated at least partially by some of the same mechanisms that are involved with CR-based lifespan extension, e.g., by the sirtuin family of genes which are thought to be involved in the CR-mediated lifespan extension response. Therefore, on this basis it is likely that an understanding of the basis or bases for CR action could result in treatments for these age related diseases in addition to methods of extending longevity.

On the basis of the above observed effects of CR on longevity and disease, considerable effort has been devoted to understanding the mechanism(s) of action of CR to produce these effects, for example by identifying the components of the CR pathway(s) by altering or mutating genes and screening for those gene alterations or mutations that change the CR response. One result of such studies has been the identification of the silent information regulator 2 (Sir2) family of protein deacetylases, also known as the sirtuins, which are found in a wide range of organisms ranging from bacteria to humans, and which have been shown to extend longevity in, e.g., yeast and the nematode worm. See, e.g., Bitterman et al., Microbiol. Mol. Biol. Rev. (2003) 67:376-399. However, other studies have shown that it is likely that there are other CR-based longevity pathways that act in parallel with those involving the sirtuins, offering up the possibility of additional pathways for interventions for increasing human longevity or reducing human disease. See, e.g., Kaeberlein et al., PLOS Biology (2004) 2:1381-1387 and Kaberlein et al., PLOS Biology (2007) 3:0655-0660 (available at plosgenetics.org); see also Medvedik et al., PLOS Biology (2007) 5:e261.

As an alternative to identifying the components of the CR pathway(s) by gene alteration or mutation, these components can also be characterized by identifying compounds that alter the CR response and then determining what molecules those compounds interact with. As noted above, although the sirtuins may be involved in the CR response, there is evidence to suggest that there are other CR-based longevity pathways, e.g., compounds unrelated to resveratrol that activate SIRT1 (identified by in vitro biochemical screen using purified SIRT1) and have important physiological effects in mice. SIRT1 is the mammalian homolog of the budding yeast silent information regulator 2 (SIR2), which encodes a histone deacetylase that has been implicated in the control of lifespan and the mitigation of age-associated diseases by CR regulatory mechanisms. See Milne et al., Nature (2007) 450:712-716. Identification of these pathways may be made by understanding the molecular effects of compounds identified as acting outside previously characterized pathways and, once identified, the components of these pathways may serve as new target molecules for modulating the CR response. See, e.g., Petrascheck et al., Nature (2007) 450:553-557.

Additionally, compound-based screens have another distinct advantage, in that the compounds identified by these screens have utility not simply for their usefulness in identifying the components of the CR pathway(s) but also because these compounds themselves, or in modified form, may be used as drugs for stimulating the CR response. Thus, for example, a compound shown in a particular model system (e.g., yeast, worms, fruit fly, mouse) to alter the CR response may be used directly, or in chemically modified form, to achieve the same result in monkeys and, ultimately, humans. The need for a variety of compounds altering the CR response is clear; resveratrol, for example, has low bioavailability and therefore is not necessarily a particularly suitable compound for altering the CR response.

One example of such a compound-based screen is the cell-based phenotypic "Death of Daughters" (DeaD) assay provided in U.S. patent application Ser. No. 10/790,456 to Goldfarb, the contents of which are herein incorporated in their entirety by reference. As described in this reference, the DeaD assay allows for the high throughput screening of compounds in yeast cells for those compounds that extend or shorten what is termed "replicative aging," i.e., aging as defined as the number of divisions an individual yeast cell undergoes before dying. In yeast, because cell division is asymmetric, it is straightforward to distinguish a newly formed small "daughter" cell from the larger "mother" cell that gave rise to the daughter by division, and therefore it is possible to monitor the number of divisions a mother cell undergoes by distinguishing these cells from their progeny. Typically this discrimination is done by a trained microscopist, and, although straightforward, is extremely labor- and time-intensive. However, the DeaD assay makes use of yeast strains that have been genetically engineered so that daughter cells die, thereby allowing for replicative assays based on the growth properties of bulk populations of cells which, because the daughters die, are essentially mothers only, i.e., methods that are quick and require relatively little labor to perform, since they are based on bulk properties (absorbance) rather than on detailed microscopic analyses.

The high throughput screening of compounds in yeast cells performed with the DeaD assay may be done on yeast cells exposed to the test compounds only; alternatively, or in addition, the DeaD assay may be done with yeast cells also treated with an agent or agents that alter longevity or other aspects of the CR response, in order to identify test compounds which counter the effects of this agent or agents. For example, the Sir2 protein, like the other sirtuins, is a $NAD^+$-dependent deacetylase which produces nicotinamide (also referred to herein as NIC or NAM) as a reaction product. Nicotinamide in turn acts as a non-competitive inhibitor of the Sir2 protein and Sir2-like enzymes in vitro and, in vivo, and can accelerate yeast ageing by inhibiting Sir2. see, e.g., Anderson et al., Nature (2003) 423:181-185. Therefore, in addition to using the DeaD assay to screen for compounds altering the CR response in untreated yeast cells, additional information on compounds altering the CR response can be obtained by using yeast cells treated with nicotinamide, i.e., in a situation where compounds are selected based on their ability to counter the longevity-shortening effects of nicotinamide.

SUMMARY OF THE INVENTION

The present invention is directed to methods for altering the lifespan of eukaryotic organisms comprising the steps of: providing a lifespan altering compound and administering an effective amount of the compound to a eukaryotic organism, such that the lifespan of the eukaryotic organism is increased.

Examples of eukaryotic organisms include single- and multi-cellular organisms, including higher-order organisms (such as mammals, which includes humans).

In one embodiment, the compound is identified using the DeaD assay as a high-throughput method to screen compounds for their effects on longevity and CR-related disease states.

In one embodiment, the compound has an EC50 of 10 μM or less. Examples of such compounds are provided as compounds 1-245 of Table 1. In another embodiment, the compound has an EC50 of 5 μM or less and examples of such compounds are provided as the first 77 compounds listed in Table 1. In yet other embodiments, the compound is selected from group of consisting of SID 14724551, SID 14732512, SID 7972147 and SID 17511642.

In one aspect, the present invention is directed to the identification of lifespan altering compounds by the high-throughput screening of compounds using the DeaD assay, including their ability to alleviate the longevity-shortening effects of nicotinamide. In another aspect, the present invention is directed to the method of use of compounds obtained by this screening. Compounds having desired criteria, such as EC50, can be selected.

In addition to the use of the particular compounds identified in, e.g., Examples 2 and 3 of the present invention, the invention is also directed to the use of compounds with common substructures or scaffolds identified by analysis of the common structural features of the compounds identified in the present invention, including, but not limited to, the scaffolds defined in FIG. 6.

The present invention is also directed to methods for isolating one or more components of the cellular pathway(s) that mediate the effects of the compounds of the present invention, with non-limiting examples of such methods provided in Example 8.

Other features and advantages of the present invention will become apparent from the following detailed description and claims and the appended drawings.

BRIEF DESCRIPTION OF THE DRAWINGS

FIG. 6A-6C provide scaffold analyses of the data of the assays of the present invention in order to identify common structural scaffolds for the active compounds defined in the assays. This figure shows 12 such scaffolds; scaffolds c1-c3 (6A), and in particular c1, have a low likelihood of occurring in the data by chance, and therefore serve as likely scaffolds for further defining compounds able to produce the results of the assays of the present invention. FIG. 6B is cc1, cc2 and cc3a and FIG. 6C is cc3b, cc4, cc5, cc6, cc7 and cc8.

FIG. 16 presents Table 1 which shows the results of 809 DeaD assay

FIG. 18 presents Table 3 which shows data for FIGS. 10-12.

FIG. 19 presents Table 4 which shows the names of Compounds 1-77 from Table 1.

DETAILED DESCRIPTION OF THE INVENTION

Figure 1:
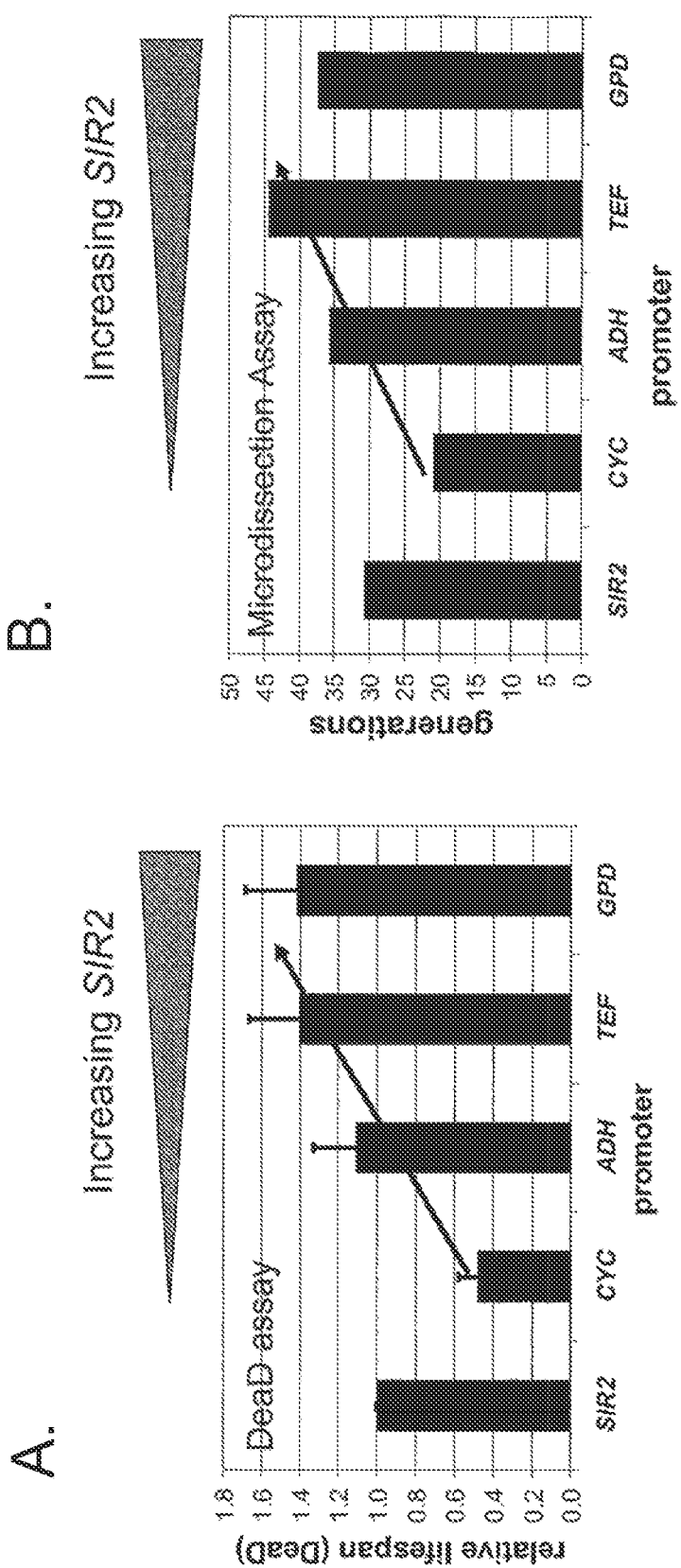
FIG. 1 provides plots demonstrating that the DeaD assay lifespan responds properly to SIR2 expression levels. Panel A: Relative DeaD lifespans are normalized to the lifespan of the parental $SIR2^+$ strain (SIR2). The integration of a series of promoters of increasing strength upstream of the chromosomal SIR2 gene shows that decreased expression (weak CYC promoter) shortens DeaD lifespan, and elevated SIR2 expression (strong TEF and GDP promoters) extend lifespan. Panel B: The same approximate results were obtained using the standard microdissection lifespan assay.

The present invention provides a method for altering the lifespan of eukaryotic organisms comprising the steps of: providing a lifespan altering compound and administering an effective amount of the compound to a eukaryotic organism, such that the lifespan of the eukaryotic organism is increased.

A lifespan altering compound ("LAC") is a compound that reverses the lifespan shortening effect of a lifespan shortening agent (such as nicotinamide or environmental agents such as paraquat) and/or increases the lifespan of a eukaryotic organism (which is not exposed to or treated with a lifespan shortening agent). Lifespan as used herein means the number of times a cell or cell population can divide (replicative lifespan) or the length of time (e.g. days or years) a cell or organism survives before dying (chronological lifespan).

The LAC may alter the lifespan through CR, dietary restriction (DR), or some other pathway. In another embodiment, the LAC reverses the effect of an agent (such as NIC) that shortens the lifespan of an eukaryotic organism. In another embodiment, a LAC increases the replicative lifespan of yeast cells in the DeaD assay. In another embodiment, a LAC increases the replicative lifespan of yeast cells in the presence or absence of a lifespan shortening agent (such as NIC). In yet another embodiment, a LAC increases the replicative lifespan of yeast cells in the presence or absence of an environmental agent (such as paraquat). In another embodiment, a LAC has an EC50 value of 5 micromolar or less in the DeaD assay. In yet another embodiment, a LAC has an EC50 value of 10 micromolar or less in the DeaD assay. In another embodiment, a LAC increases the lifespan of an higher organism such as *C. elegans*. In yet another embodiment, a LAC increases the lifespan of a mammal such as a human.

An effective amount of a LAC increases or decreases the lifespan of an eukaryotic organism. In one embodiment, an effective amount of a LAC increases the lifespan of an eukaryotic organism by a statistically significant amount compared to the lifespan of an untreated organism. The lifespan of an untreated organism may be determined in parallel or may be obtained from separately conducted studies (control). In another embodiment, an effective amount of a LAC increases the lifespan of an eukaryotic organism by at least 5%. In other embodiments, an effective amount of a LAC increases the lifespan of an eukaryotic organism by at least 10, 15, 20, 25, 35, 50%, or 100% over control.

Examples of eukaryotic organisms include single- and multi-cellular organisms, including higher-order organisms (such as mammals, which includes humans).

In one embodiment, the present method can be used in order to generally increase the lifespan of the cells of a eukaryotic organism and to protect its cells against stress and/or against apoptosis. While not intending to be bound by any particular theory, it is believed that use of the present method is similar to subjecting the subject to hormesis, i.e., mild stress that is beneficial to organisms and may extend their lifespan.

In various other embodiments, the present method can be used for treating or preventing a disease or condition induced or exacerbated by cellular senescence in a subject; for extending the lifespan of a subject; for treating or preventing a disease or condition relating to lifespan; for treating or preventing a disease or condition relating to the proliferative capacity of cells; for treating or preventing a disease or condition resulting from cell damage or death.

In various embodiments, the present method may be used to prevent aging and aging-related consequences or diseases, such as stroke, heart disease, heart failure, arthritis, high blood pressure, and Alzheimer's disease. Other conditions that can be treated include ocular disorders, e.g., associated with the aging of the eye, such as cataracts, glaucoma, and macular degeneration. The present method may also be used to treat chronic diseases associated with cell death in order to protect the cells from cell death. Exemplary diseases include those associated with neural cell death, neuronal dysfunction, or muscular cell death or dysfunction, such as Parkinson's disease, Alzheimer's disease, multiple sclerosis, amniotropic lateral sclerosis, and muscular dystrophy; AIDS; fulminant hepatitis; diseases linked to degeneration of the brain, such as Creutzfeld-Jakob disease, retinitis pigmentosa and cerebellar degeneration; myelodysplasis such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections. Cell death can also be caused by surgery, drug therapy, chemical exposure or radiation exposure.

The present method may also be used to treat acute diseases, e.g., damage to an organ or tissue, e.g., a subject suffering from stroke or myocardial infarction or a subject suffering from a spinal cord injury or may also be used to repair an alcoholic's liver.

In one embodiment, the invention provides a method extending the lifespan of a eukaryotic cell, extending the proliferative capacity of a eukaryotic cell, slowing ageing of a eukaryotic cell, promoting the survival of a eukarotic cell, delaying cellular senescence in a eukaryotic cell, mimicking the effects of calorie restriction, increasing the resistance of a eukaryotic cell to stress, or preventing apoptosis of a eukaryotic cell, by contacting the cell with a compound of the present invention.

For example, the methods described herein may be used to increase the amount of time that eukaryotic cells, particularly primary eukaryotic cells (i.e., cells obtained from an organism, e.g., a human), may be kept alive in a cell culture. Embryonic stem (ES) cells and pluripotent cells, and cells differentiated therefrom, may also be treated with a compound of the present invention to keep the cells, or progeny thereof, in culture for longer periods of time. Such cells can also be used for transplantation into a subject, e.g., after ex vivo modification.

As another example, eukaryotic cells that are intended to be preserved for long periods of time may be treated using the method of the present invention. The cells may be in suspension (e.g., blood cells, serum, biological growth media, etc.) or in tissues or organs. For example, blood collected from an individual for purposes of transfusion or blood to be used for forensic activity may be treated using the present invention to preserve the blood cells for longer periods of time. Other cells that may be treated to extend their lifespan or protect against apoptosis include cells for consumption, e.g., cells from non-human mammals (such as meat) or plant cells (such as vegetables).

As yet another example, the method of the present invention may also be applied during developmental and growth phases in mammals, plants, insects or microorganisms, in order to, e.g., alter, retard or accelerate the developmental and/or growth process.

As yet another embodiment, the present method can be used to treat cells useful for transplantation or cell therapy, including, for example, solid tissue grafts, organ transplants, cell suspensions, stem cells, bone marrow cells, etc. The cells or tissue may be an autograft, an allograft, a syngraft or a xenograft. The cells or tissue may be treated according to the present method prior to administration/implantation, concurrently with administration/implantation, and/or post administration/implantation into a subject. The cells or tissue may be treated prior to removal of the cells from the donor individual, ex vivo after removal of the cells or tissue from the donor individual, or post implantation into the recipient.

As yet another example, cells may be treated using the method of the present invention to increase their lifespan or prevent apoptosis. For example, skin can be protected from aging (e.g., developing wrinkles, loss of elasticity, etc.) by treating skin or epithelial cells with the method of the present invention. Exemplary skin afflictions or skin conditions that may be treated in accordance with the methods described herein include disorders or diseases associated with or caused by inflammation, sun damage or natural aging. For example, the present method can find utility in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In another embodiment, the method of the present invention may be used for the treatment of wounds and/or burns to promote healing, including, for example, first-, second- or third-degree burns and/or a thermal, chemical or electrical burns.

It is expected that the compound can be delivered to a eukaryotic organism using any available method and route suitable for compound delivery, including oral, parenteral, subcutaneous, intraperitoneal, intrapulmonary, and intranasal routes. It will be recognized by those of skill in the art that the form and character of the particular dosing regimen employed in the method of the invention will be dictated by the route of administration and other well-known variables, such as the size and age of the eukaryotic organism. Determination of such dosing regimens is within the purview of one skilled in the art. Administration of the compound could be performed in conjunction with any conventional therapies that are intended to treat a disease or disorder associated with aging including topical, oral, or injectable. Administration of the LAC can also be done by exposing or contacting the cell or cells to an environment (such a growth or culture medium) containing an effective amount of a LAC.

In one embodiment, the compound is identified using the DeaD assay as a high-throughput method to screen compounds for their effects on longevity and CR-related disease states. Other embodiments include, use of these compounds to more precisely identify the structural features of these compounds that are responsible for their activity, methods of identifying the cellular pathway(s) that mediate the activity of these compounds, and methods of extrapolating these results to higher organisms.

In the present invention, "activity" refers generally to the ability of a compound to exert a CR effect, or a CR-like effect. The precise meaning of "activity" depends upon the assay used, for example, whether the assay involves a single concentration of nicotinamide (Example 2) or multiple concentrations of this compound as are required to define an EC50 activity (Example 3). Thus, "activity" as used herein, encompasses both of these meanings.

In various embodiments, the LAC is selected from the compounds of Table 1. These compounds are identified by their SID (substance identifier) number which is readily recognized by those having skill in the art. The SID number is a field in the PubChem database of chemical molecules maintained by the National Center for Biotechnology Information (NCBI), a component of the National Library of Medicine, which is part of the United States National Institutes of Health (NIH).

In various embodiments the LAC is selected from the first 77 compounds listed in Table 1. These IUPAC and common names of the first 77 compounds listed in Table 1 are listed in Table 4. Further, Compound 15 from Table 4 has the following structure:

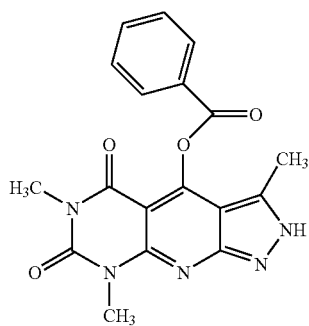

Compound 15

In various embodiments, the compound is selected from the group consisting of the compounds listed in Table 2. In various embodiments, the compound is selected from group of consisting of SID 14724551, SID 14732512, and SID 17511642.

The following non-limiting Examples provide further description of the present invention.

Example 1

Validation of the DeaD Assay

Figure 2:
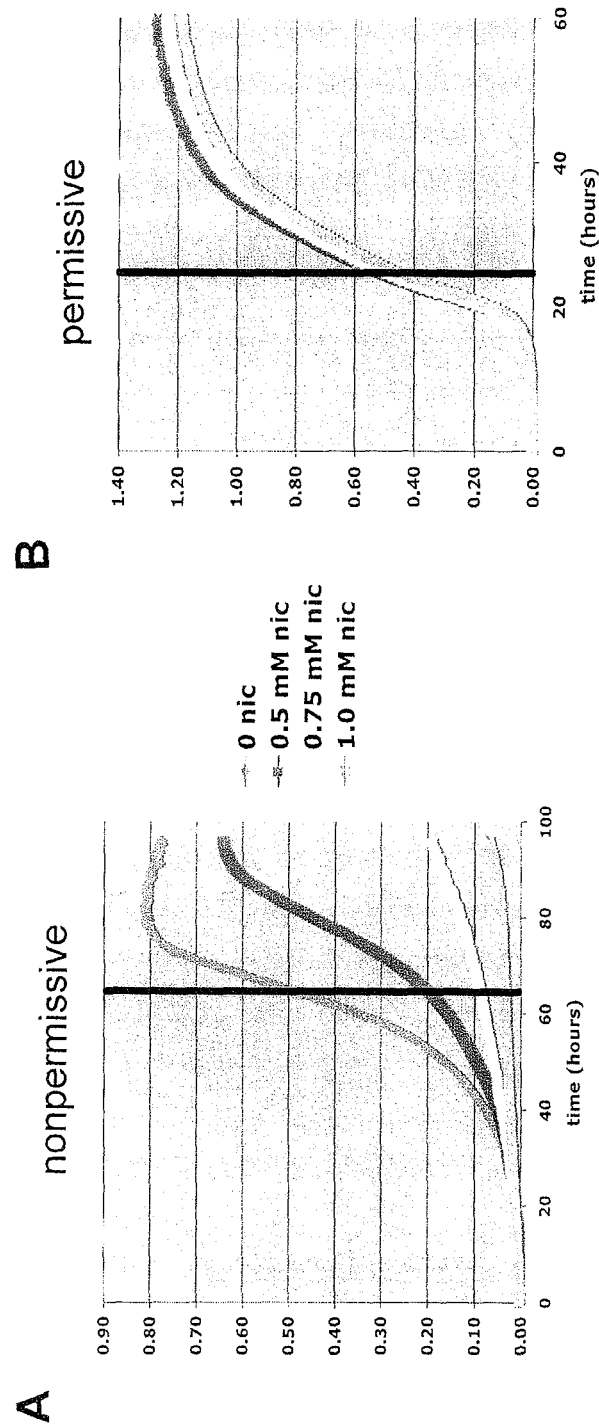
FIG. 2 provides plots demonstrating that DeaD lifespan is reduced by nicotinamide. Panel A: Under growth in glucose (nonpermissive conditions) DeaD lifespans are reduced in a dose-dependent fashion by increasing concentrations of nicotinamide. Panel B: Under growth in galactose (permissive conditions) these concentrations of nicotinamide do not alter growth. The lines shown in panel A correspond to (top to bottom) 0, 0.5, 0.75, and 1 mM NIC. The 3 lines visible in panel B correspond to (topmost to bottommost), 0.5, 0.75, or 1 mM NIC; the 0 mM NIC line is not visible.

The DeaD assay was developed as a high throughput proxy for conventional microdissection assays used to determine yeast replicative ageing. In order to verify the ability of this assay to produce results corresponding to conventional microdissection assay results, the data of FIG. 1 were obtained using either the DeaD assay (panel A) or via microdissection (panel B). As this figure shows, increased SIR2 expression increases lifespan similarly between the DeaD assay and conventional microdissection. FIG. 2 shows additional confirmation of the validity of the DeaD assay; specifically, the data of FIG. 2 show that nicotinamide reduces the lifespan of the DeaD strain in a dose-dependent fashion (panel A) without altering growth under permissive conditions (panel B). These data thus confirm the general applicability of the DeaD assay as a high throughput proxy for conventional microdissection assays of test compounds, and open the door to the use of the DeaD assay for high throughput screening of compound libraries, as will be discussed below.

Example 2

The "775" DeaD Assay Initial Screen of about 132,000 Compounds for the Ability to Counter Nicotinamide Lifespan Shortening Having established the suitability of the DeaD assay as a proxy for microdissection, the DeaD assay was used to screen a 132,796 compound library for the ability of compounds in the library to counter the lifespan-shortening effect of nicotinamide.

Specifically, as described in the AID 775 assay results (synonymously, the "775" assay results) on the "PubChem" website at pubchem.ncbi.nlm.nih.gov/assay/assay.cgi?aid=775, the contents of which are herein incorporated in their entirety by reference, the percent inhibition of nicotinamide lifespan shortening, i.e. percent reversal of nicotinamide effect on lifespan, was calculated using the optical density in control wells with cells treated with 1.5 mM nicotinamide as full lifespan shortening effect of nicotinamide (0% inhibition of nicotinamide), and wells with cells grown in medium without nicotinamide as an indicator of 100% inhibition. The appropriate compounds in the PubChem compound library (about 132,000 compounds selected from the total library of about 10 million compounds) were screened at 10 uM in the presence of 1.5 mM nicotinamide. For further details, see, e.g., the following references: Jarolim, S., Millen, J., Heeren, G., Laun, P., Goldfarb, D. S. and M. Breitenbach. (2004). A novel assay for replicative lifespan in Saccharomyces cerevisiae. FEMS Yeast Res. 5, 169-177; Bitterman, K. J., Anderson, R. M., Cohen, H. Y., Latorre-Esteves, M., and D. A. Sinclair. (2002). Inhibition of silencing and accelerated aging by nicotinamide, a putative negative regulator of yeast Sir2 and human SIRT1. J. Biol. Chem. 277, 45099-45107; Tsuchiya, M., Dang, N., Kerr, E. O., Hu, D., Steffen, K. K., Oakes, J. A., Kennedy, B. K. and M. Kaeberlein (2006) Sirtuin-independent effects of nicotinamide on lifespan extension from calorie restriction in yeast. Aging Cell. 5, 505-514.

Protocol

Assays were conducted as follow. Cells were streaked out on a YPGal agar plate and grown for 48 hours at 30° C. Four colonies were selected, 50 mL of YPGal medium in a flask was inoculated and grown at 30° C. with shaking O/N. OD600 was measured. The OD should be <0.7 for the cells to be in log phase. The cells were centrifuged, washed once and resuspended in CSMM-D restrictive growth medium. OD600 was measured again. The culture was diluted to an OD600 of 0.002 in CSMM-D restrictive medium. The culture was pre-incubated in a flask with shaking at 30° C. for 4 hours. At the end of the pre-incubation, OD600 was measured for reference. Nicotinamide (negative control), medium alone (positive control) and compounds in the presence of nicotinamide were plated with DMSO at 10× concentration (final concentrations: nicotinamide 1.5 mM, compounds 10 uM, DMSO 0.25%) in 384-well plates: 5 uL/well. The yeast was added to the plates: 45 uL/well. Plates were incubated at 30 C in a humidified chamber. After 48 hours incubation, plates were shaken for 30 seconds and OD615 was read in an EnVision (PerkinElmer) multilabel plate reader. For these assays, YPGal medium was prepared as 10 grams yeast extract, 20 grams peptone, 900 mL water, autoclave at 121° C. for 15 minutes, add 100 mL sterile 20% (w/v) galactose. CSMM-D (Complete Synthetic Minimal Medium-Dextrose) (restrictive) medium was prepared as 6.7 grams yeast nitrogen base without amino acids, 2.0 grams Drop-out mix complete (DOC) (USBiological Cat. no. D9515), 100 mL 20% (w/v) dextrose, water to 1.0 L, then filter sterilize.

Results

An activity threshold of >26% was calculated as greater than three standard deviations from the median compound inhibition. Therefore, compounds that exhibited >26% inhibition are defined as active. Compounds that exhibited <=26% inhibition are defined as inactive. Because of the inherent error in all high-throughput screens including the fallacy of over-interpreting single dose data, a tiered scoring system was adopted for this Example, in which compounds were scored on a scale of 0-40 based on activity, with a scaled activity threshold of 11. Using this tiered scoring system, the compounds were ranked, with 906 of these compounds defined as "active" using this tiered scoring system. The detailed listing of the active and inactive compounds identified in this Example are provided via the "show results" link at pubchem.ncbi.nlm.nih.gov/assay/assay.cgi?aid=775. See ncbi.nlm.nih.gov/sites/entrez in general to determine the chemical structures and IUPAC designators corresponding to these compounds; see also ncbi.nlm.nih.gov/sites/entrez?db=pcassay&cmd=Link&LinkName=pcassay_pcompound&from_uid=775 for the specific chemical structures and IUPAC designators corresponding to compounds of this Example.

Discussion

The data of this Example define about 900 compounds showing "activity" in overcoming nicotinamide inhibition as judged by the criteria provided above. Such "activity" is a useful criterion for measuring the ability of a compound to overcome nicotinamide inhibition, however, it is only one such measure of "activity." Thus, this criterion should be supplemented with, e.g., the effect of a compound's dose-dependency (see Example 3 below), the effect of a compound using microdissection assays, etc.

Example 3

The "809" DeaD Assay Screen of the Dose-Dependencies of the Top 500 Compounds Identified in Example 1 to Obtain a 50% Effective Concentration (EC50) Value As already discussed, Example 2 provides data using the "775" DeaD assay to determine compounds that counter the lifespan-reducing effects of 1.5 mM nicotinamide, with this Example identifying about 900 "active" compounds. Example 2 used only a single compound concentration of 10 uM; in the current Example, the top 500 of these "active" compounds were again screened using the DeaD assay, but now at 8 concentrations ranging from 0.078 to 10 uM, again in the presence of 1.5 mM nicotinamide, resulting in the data provided in Table 1. This more extensive data allowed for the determination of the half maximal effective concentration (EC50). See the "AID 809" assay (the "809" assay) results on the PubChem website at pubchem.ncbi.nlm.nih.gov/assay/assay.cgi?aid=809.

Thus, in this Example compounds were screened in an 8-point 2-fold dilution series ranging from 0.078 to 10 uM in the presence of 1.5 mM nicotinamide. The percent activation of lifespan, i.e. percent reversal of nicotinamide effect on lifespan, was calculated using the optical density in control wells with cells treated with 1.5 mM nicotinamide as full lifespan shortening effect of nicotinamide (0% activation), and wells with cells grown in medium without nicotinamide as an indicator of 100% activation. From the % activation values of the different compound concentrations, the half maximal effective concentration (EC50) was calculated using IDBS ActivityBase software and XLfit equation 205 for a four parameter logistic fit; the maximum and minimum values were fixed at 100% and 0%.

Protocol

Assays were conducted as follow. Cells (DeaD strain BB579) were streaked out on a YPGal agar plate and grown for 48 hours at 30° C. Four colonies were selected, 50 mL of YPGal medium in a flask was inoculated and grown at 30 C with shaking O/N. OD600 was measured. The OD should be <0.7 for the cells to be in log phase. The cells were centrifuged, washed once and resuspended in CSMM-D restrictive growth medium. OD600 was measured again. The culture was diluted to an OD600 of 0.002 in CSMM-D restrictive medium. The culture was pre-incubated in a flask with shaking at 30° C. for 4 hours. At the end of the pre-incubation, OD600 was measured for reference. Nicotinamide (negative control), CSMM-D medium alone (positive control) and compounds in the presence of nicotinamide were plated with DMSO at 10× concentration (final concentrations: nicotinamide 1.5 mM, compounds 0.078-10 uM, DMSO 0.5%) in 384-well plates: 5 uL/well. The yeast was added to the plates: 45 uL/well. Plates were incubated at 30° C. in a humidified chamber. After 48 hours incubation, plates were shaken for 30 seconds and OD615 was read in an EnVision (PerkinElmer) multilabel plate reader. For these assays, YPGal medium was prepared as 10 grams yeast extract, 20 grams peptone, 900 mL water, autoclave at 121° C. for 15 minutes, add 100 mL sterile 20% (w/v) galactose. CSMM-D (Complete Synthetic Minimal Medium-Dextrose) (restrictive) medium was prepared as 6.7 grams yeast nitrogen base without amino acids, 2.0 grams Drop-out mix complete (DOC) (USBiological Cat. no. D9515), 100 mL 20% (w/v) dextrose, water to 1.0 L, then filter sterilize.

Results

An activity threshold of EC50<=10 uM was set and compounds that met this criterion are defined as active. Compounds that exhibited an EC50>10 uM are defined as inactive.

A tiered scoring system was applied to the data, as is shown in the "Rank Score" column of Table 1, which shows the results obtained for these 500 compounds. In this system, active compounds were scored on a scale of 41-80 using an inverted linear correlation to EC50s between 0 and 10 uM. Compounds that did not confirm as actives in the dose response screen were given the score 0.

As shown in Table 1, 77 of the 500 compounds tested yielded EC50 values below 5 uM (i.e., #s 1-77 in Table 1), with these 77 compounds therefore considered active by this EC50 criterion. In order to validate these results for more than the single measured optical density at 600 nm obtained at a 48 hr time point in this Example and shown in Table 1, full DeaD lifespan timecourses were performed for these roughly top 70 compounds, as shown in Example 4 below.

Example 4

Full DeaD Assay Lifespan Timecourses for the Approximately Top 70 Compounds Identified in Example 3

Figure 3:
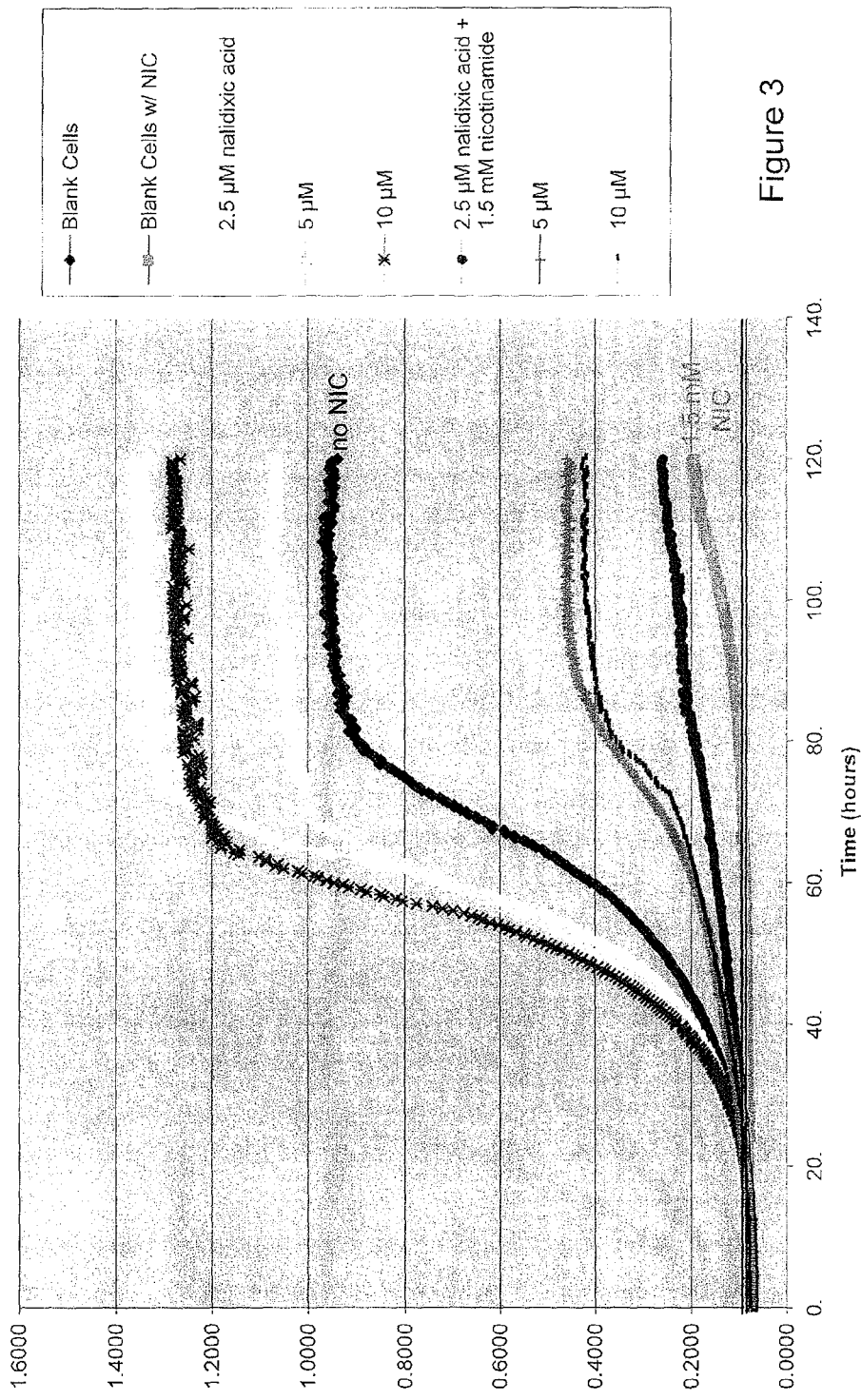
FIG. 3 provides a plot showing DeaD assays for compound SID 855620 (nalidixic acid) in the presence and absence of nicotinamide. The nalidixic acid was incubated with growing cells under nonpermissive conditions at concentrations of 2.5, 5.0, and 10 uM (micromolar) in the presence and absence of 1.5 mM nicotinamide. Control experiments for growth in the presence and absence of nicotinamide without the drug are included. The last three entries showing the line labeling are all results obtained with 1.5 mM nicotinamide and, respectively, 2.5, 5 or 10 uM nalidixic acid. The data lines shown in this figure correspond to (topmost to bottommost as they appear at the extreme right side of the data lines): 2.5, 10, or 5 uM nalidixic acid (no nicotinamide); blank cells (labeled "no NIC"); 5 or 10 uM nalidixic acid plus 1.5 mM nicotinamide (in both cases); 10 uM nalidixic acid (no nicotinamide); and, blank cells with 1.5 mM nicotinamide (labeled "1.5 mM NIC").
Figure 5:
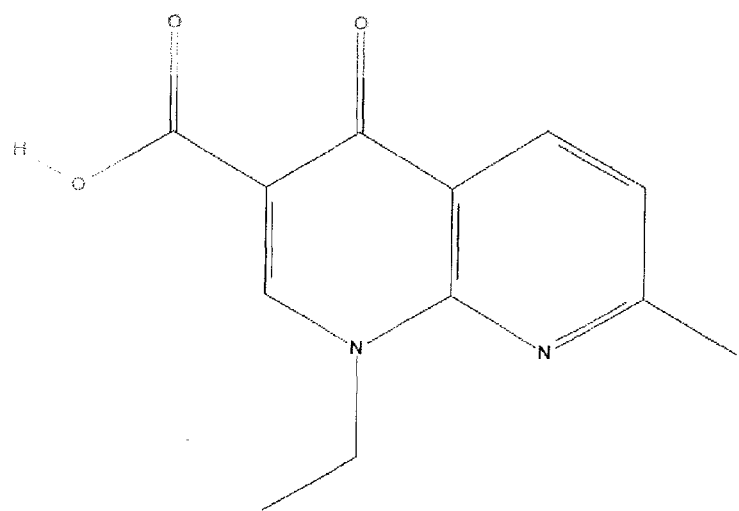
FIG. 5 provides the structure of nalidixic acid, a synthetic 1,8-naphthyridine antimicrobial agent with a limited bacteriocidal spectrum that is an inhibitor of the A subunit of bacterial DNA gyrase.

In order to validate the results of the "809" experiment of Example 3, timecourses for the effect of the top 70 compounds identified in Example 3 may be performed using the DeaD assay for, e.g., a 140 hour interval for each of these compounds. FIG. 3 provides exemplary data of such an experiment that was performed using compound #52 of Table 1, nalidixic acid (SID #855620; see FIG. 5 for the structure of this compound), a compound that is a known inhibitor of topoisomerase II and is an approved antimicrobial drug for human use. As this figure shows, nalidixic acid extends DeaD lifespan both in the presence and absence of nicotinamide. Data for the other compounds apart from nalidixic acid may be similarly obtained.

Example 5

Microdissection Results to Verify the Data of Example 4 for Nalidixic Acid

Figure 4:
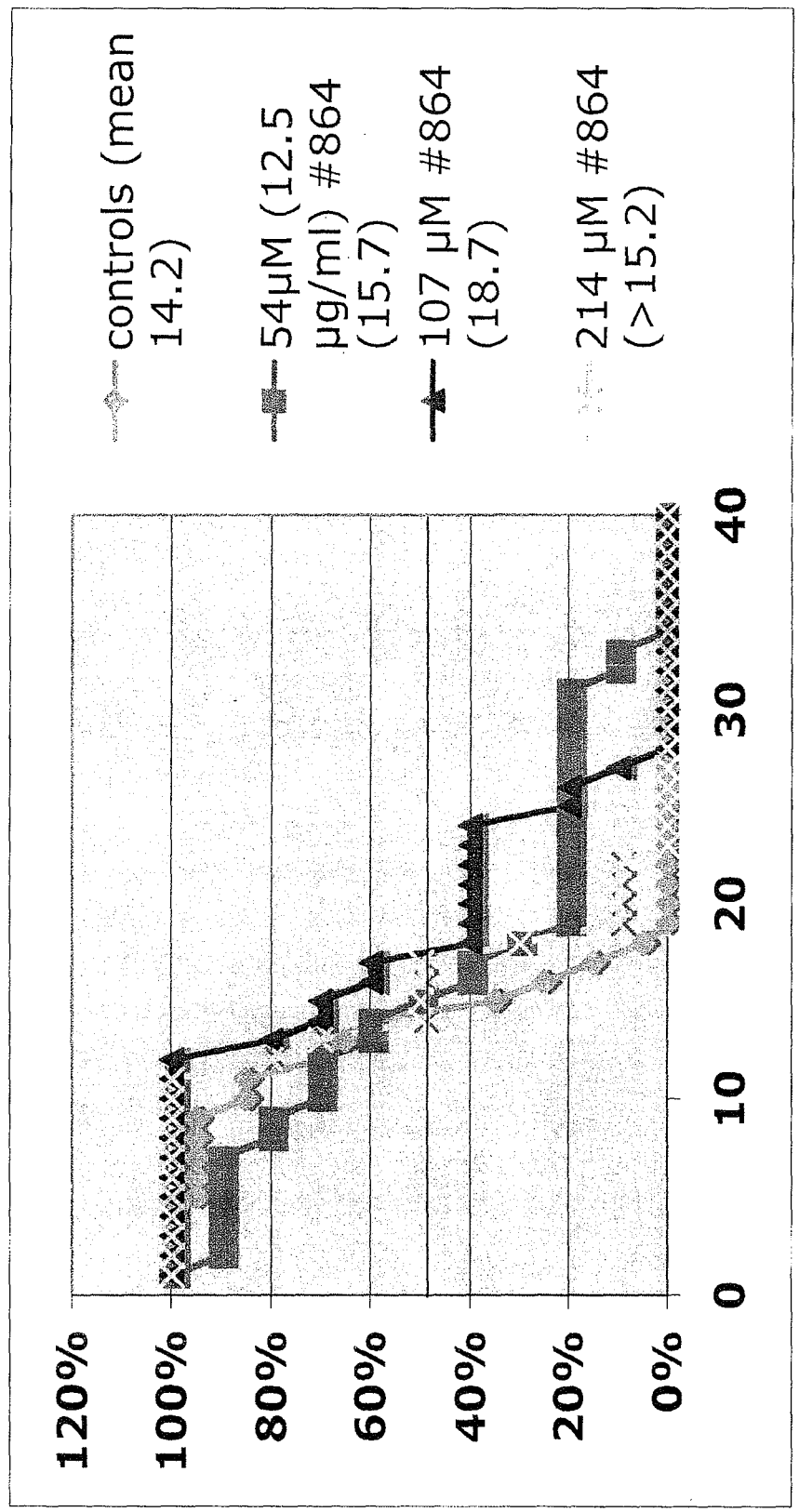
FIG. 4 provides standard microdissection lifespans for nicotinamide in the presence of nalidixic acid and 5 mM nicotinamide. Three experiments that included three concentrations of nalidixic acid all increased mean lifespans (shown in parentheses) and maximum lifespans. In this Figure, "#864" refers to nalidixic acid, e.g., the second entry in the legend refers to 54 uM nalidixic acid, the third entry refers to 107 uM nalidixic acid, etc. The number presented in parentheses in the figure legend refers to the mean lifespan of the population in each experiment presented in this Figure, e.g., the control population (5 mM nicotinamide only) has a mean lifespan of 14.2 generations, etc.

In order to verify the data of Example 4 for nalidixic acid, microdissection experiments were performed using this compound to counter the effect of nicotinamide, with the results of these experiments shown in FIG. 4.

Example 6

Microdissection Results to Verify the Data of Example 4 for the Other (Non-Nalidixic Acid) Top 70 Compounds Identified in Example 3

In order to verify the data of Example 4 for the top 70 compounds of Example 3 other than nalidixic acid, microdissection assays are performed, and results are obtained using controls and experimental conditions as provided for the experiments of FIG. 4.

Example 7

Scaffold Analysis

As stated previously, the lifespan assays of the present invention are useful for defining compounds that alter longevity in yeast, and by the likely conservation of these mechanisms during evolution as supplemented by, when necessary, experimental validation of data obtained in yeast to higher organisms, to higher organisms including humans. See also Example 9 below.

More specifically, the Examples given above provide compound screens in yeast using the DeaD assay that define a small active subset of about 70 compounds of the original approximately 132,000 originally screened, where activity is defined by EC50 in the DeaD assays as discussed above.

These compounds, by themselves, provide potential drug molecules for intervention in altering longevity or diseases associated with the CR effect, as well as molecules that may be used to identify potentially previously uncharacterized or unknown CR pathways. However, it is particularly advantageous to extrapolate from these particular compounds to identify the key functional aspect(s) of these molecules that underpin their activity in the DeaD assays given in the previous Examples, e.g., functional moieties or other activity-conferring chemical structures, scaffolds, side-groups, etc. that are responsible for the interaction(s) of these compounds with the cellular pathways mediating the effects seen in the DeaD assays.

In order to obtain such information regarding the key features of the active molecules defined in the Examples, a scaffold analysis was performed on the data of these Examples, with the results of this analysis provided in FIG. 6.

Thus, for example group "c1" of FIG. 6 refers to the chemical scaffold shown in the c1 row of FIG. 6. As FIG. 6 shows, this scaffold is found as a substructure (i.e., in its complete form within a compound comprising at least this structure, but generally containing further chemical structure) of 3 "active" hits of the assays of the present invention. The likelihood of this occurring can be calculated to be relatively rare; therefore, there is a reasonable probability that the c1 scaffold is important for the interaction(s) of the active compounds of the invention with the cellular mechanisms mediating the activity of these compounds.

Further explication of the results shown in FIG. 6 may be made via the PubChem website. For the c1 group, for example, the scaffold shown for this group may be entered as the SMILES string C1(CC(CC(C1C(C)=O)=O)C)=O in the search input field of http://pubchem.ncbi.nlm.nih.gov/search/search.cgi (SMILES/STARTS format) and then searched from this page with "Search Type" set to "Substructure." This search identifies 351 compounds in the entire PubChem database of about 10 million compounds (of which about 132,000 were used for the activity assays of the present invention; see above) as containing this substructure.

Figure 7:
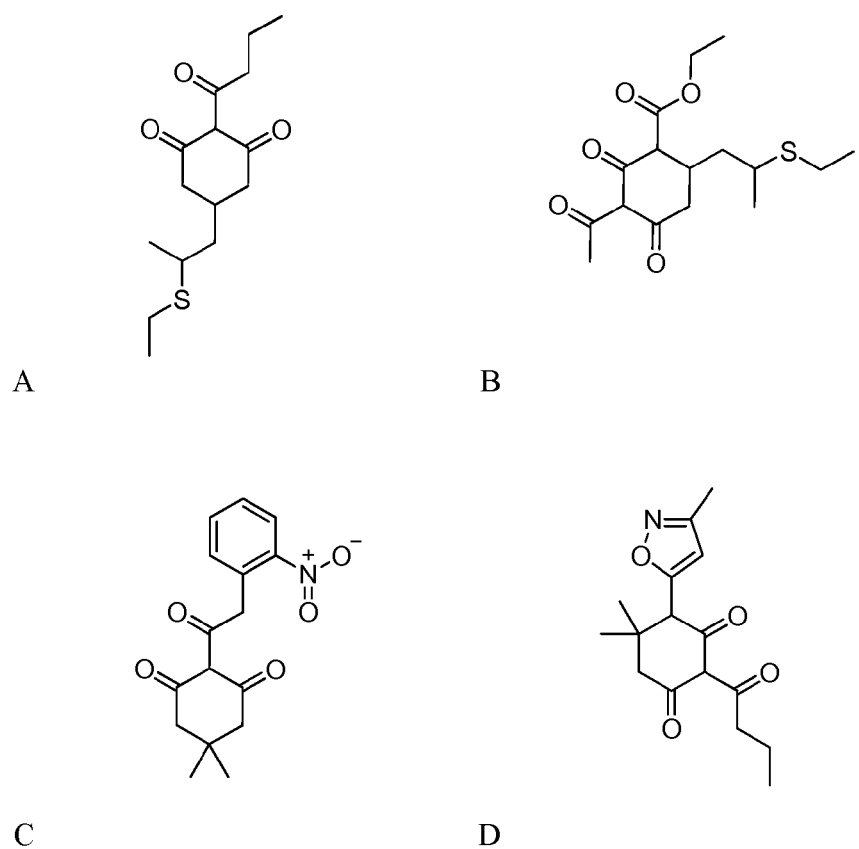
FIG. 7 provides the structures of SIDs A) 14732512, B) 14724551, C) 17511642, and D) 7972147 containing the c1 scaffold and identified in the 775 assay as "active."
Figure 8:
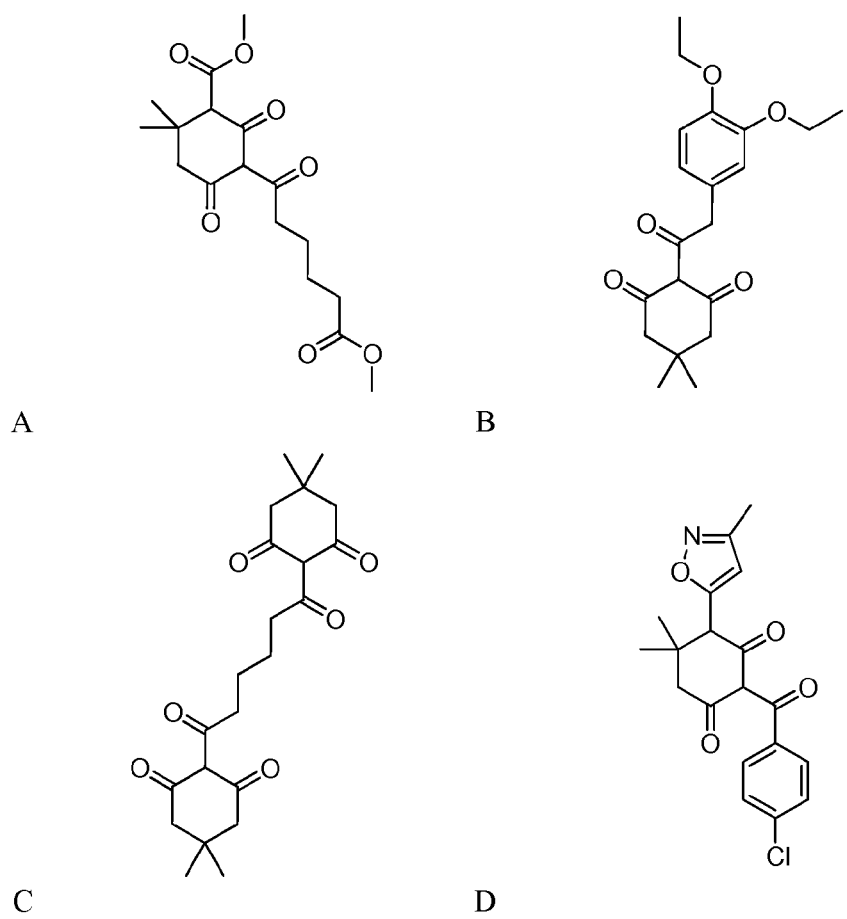
FIG. 8 provides the structures of SIDs A) 7972920, B) 14732962, C) 4245034, and D) 842694 containing the c1 scaffold and identified in the 775 assay as "inactive."

Of these 351 compounds, 21 are found in PubChem bioactivity assays. This latter group may be displayed by clicking on the "BioAssay" tab of the PubChem page displayed after the search is conducted and then changing the "Display" dropdown format from "Summary" to "PubChem BioActivity Summary." There are 4 compounds containing the c1 substructure that were identified in the 775 assay as active and 4 additional compounds identified in that assay as inactive, where "active" and "inactive" are definitions specific to the 775 assay (see the "Results" section of Example 2 above). These specific compounds may be displayed by clicking on the numeric entries displayed in the PubChem result obtained as above; in the present application, these results are presented as FIGS. 7 and 8, respectively, with the PubChem Substance ID ("SID") numbers for these compounds provided in the legends to the figures.

Figure 9:
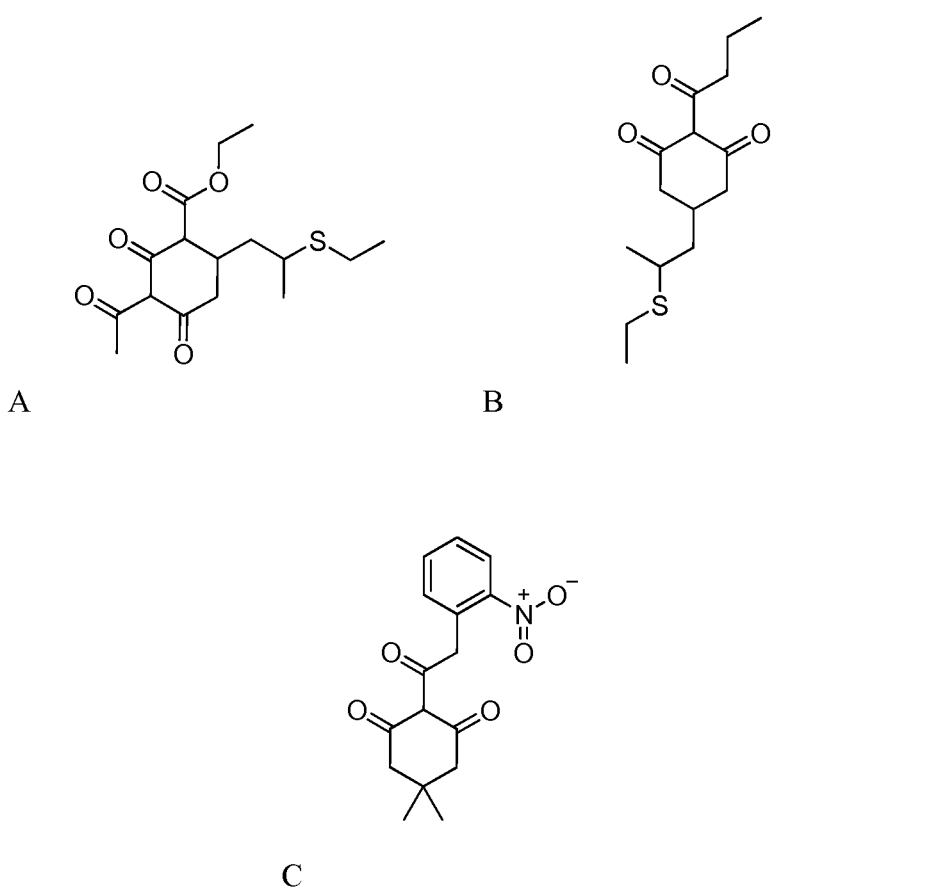
FIG. 9 provides the structures of SIDs A) 14724551, B) 14732512, and C) 17511642 containing the c1 scaffold and identified in the 809 assay as "active."

Similarly, FIG. 9 provides the SIDs of the three compounds containing the c1 scaffold and identified as "active" in the 809 assay. Note that these compounds all were also identified as active in the 775 assay (i.e., that the three compounds in FIG. 9 are also shown in the results summarized in FIG. 7). Also note that the compounds in FIG. 9 correspond to the row entries in the 809 assay results of Table 1 as follow: SID 14724551 (FIG. 9A) appears in Table 1, row 21; SID 14732512 (FIG. 9B) appears in Table 1, row 25; and, SID 17511642 (FIG. 9C) appears in Table 1, row 66.

As discussed above, the data in this Example are directed to identifying a common chemical structure or scaffold from the activity assay results of the previous Examples, so that this scaffold may be used to 1) find additional compounds having activity, and ideally higher activity and/or selectivity, and 2) to use these refined chemical structure data to better design compounds to identify the cellular pathways that these compounds interact with to produce their activity effect(s).

Thus, with regard to the identification of additional compounds, scaffold c1 for example defines a common structure shared by three compounds having high activity in, e.g., the 809 assay, with these three compounds shown in FIG. 9. This information may be used to select additional compounds from the PubChem database containing the c1 structure, or variants of the c1 structure, in order to define which of the chemical groups in this structure underpin the activity displayed by the compounds having this common scaffold. For example, removal of one or more of the C=O moieties in c1, substitution of these moieties with other groups, etc., could be used to characterize the contribution of each of these C=O moieties to the overall binding of compounds containing the c1 group.

Example 8

Pathway Identification

The compounds of the present invention may be used directly to treat disease, extend longevity, etc., either in their present form or in varied forms as would be designed by, e.g., a medicinal chemist (see also Example 9 below). These compounds may additionally be used to identify the pathway(s) which mediate their activities in vivo, since, as already discussed, knowledge of these pathways would allow for the design of other compounds interacting with these pathways, or for compounds interfering with the normal interactions of the components of these pathways, etc.

With regard to the use of the compounds of the invention to identify cellular pathways, one of ordinary skill would recognize a large number of techniques to identify these pathways. Such techniques include, but are not limited to: genetic techniques where yeast mutant libraries are used to determine what yeast mutations abolish the activity of the compounds of the invention; direct techniques, such as techniques were cell extracts are screened for binding to the compounds of the invention (or to variants of these compounds, compounds derived from the defined scaffolds of FIG. 6, etc.); other methods of direct binding; etc.

Example 9

Assays in Higher Eukaryotic Organisms

The previous Examples are directed to the use of the DeaD assay and microdissection assay in yeast. There is extensive data to suggest that such results are likely applicable to higher eukaryotic organisms, including humans, in light of the generally highly-conserved nature of the CR pathways. Furthermore, even without direct experimental data, results in yeast may likely be extrapolated to higher organisms on the basis of in silico analyses of the yeast results against data for other model system. Thus, for example, particularly pathways defined in yeast as the targets of the compounds identified in the previous Examples may be compared in silico against data for higher organisms to determine whether the genes for such pathways exist in those higher organisms, whether the interactions of the proteins/nucleic acids in those pathways are likely the same in higher organisms as they are in yeast, etc.

In addition, experimental studies may be performed in higher organisms to extend the results obtained in the present application for the yeast model system. Thus, for example, considerable effort has gone into developing worm, fruit fly, etc., model systems for CR effects (see the Background section of the present application, and the references cited therein), and these model systems may be used to validate or extend the results obtained in the preceding Examples for the compounds obtained in these Examples.

In this regard, for example, the techniques used in Petrascheck et al. (Nature (2007) 450:553-557), may be used to extend the results described above to nematodes. Additional methods as would be known to one of ordinary skill may also be employed in this regard.

Example 10

Additional Compound DeaD and Microdissection Assays

Figure 10:
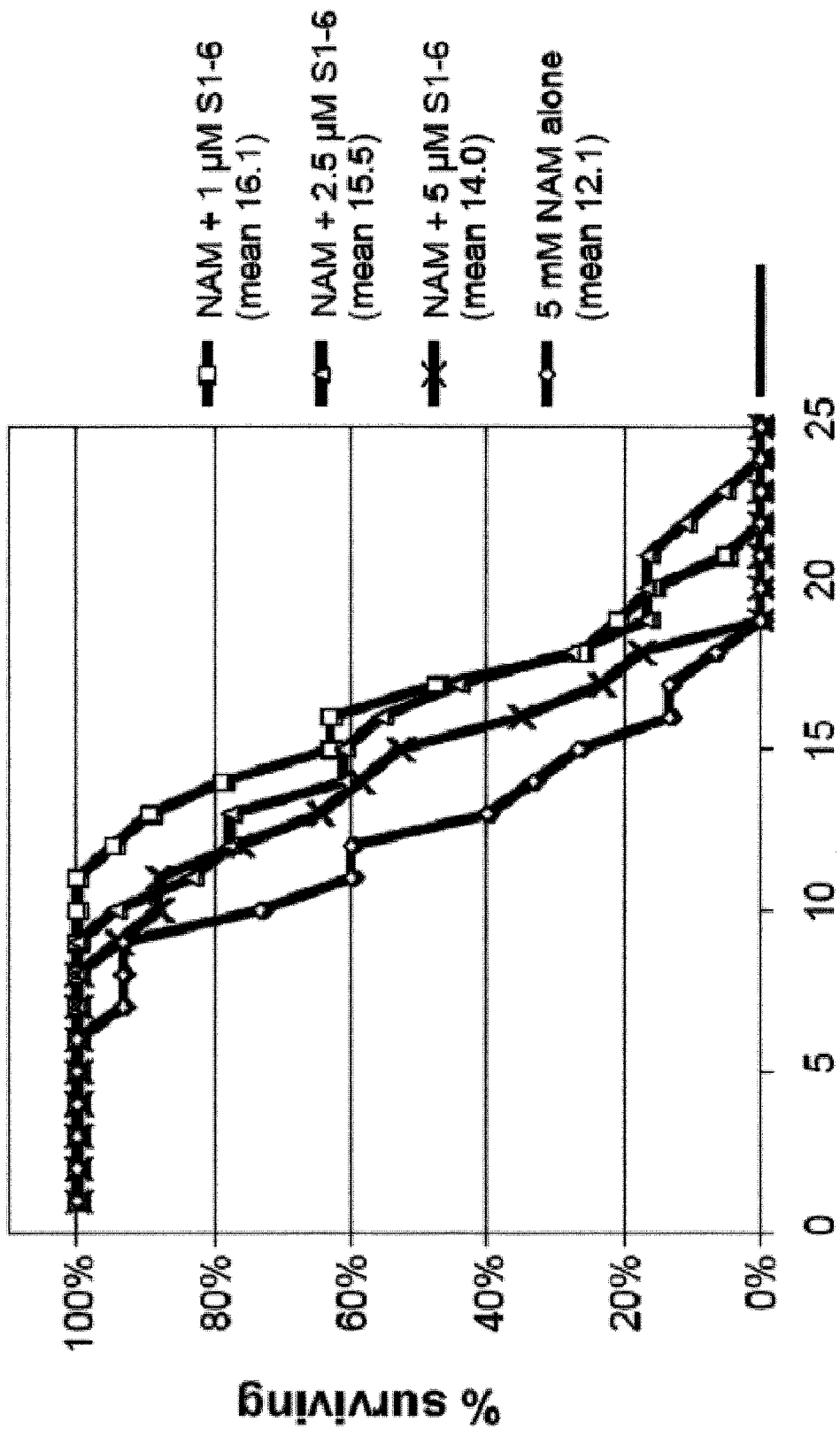
FIGS. 10-12 provide microdissection assays for a number of the compounds presented in Table 2. Table 3 provides the data used to generate FIGS. 10-12.
Figure 11:
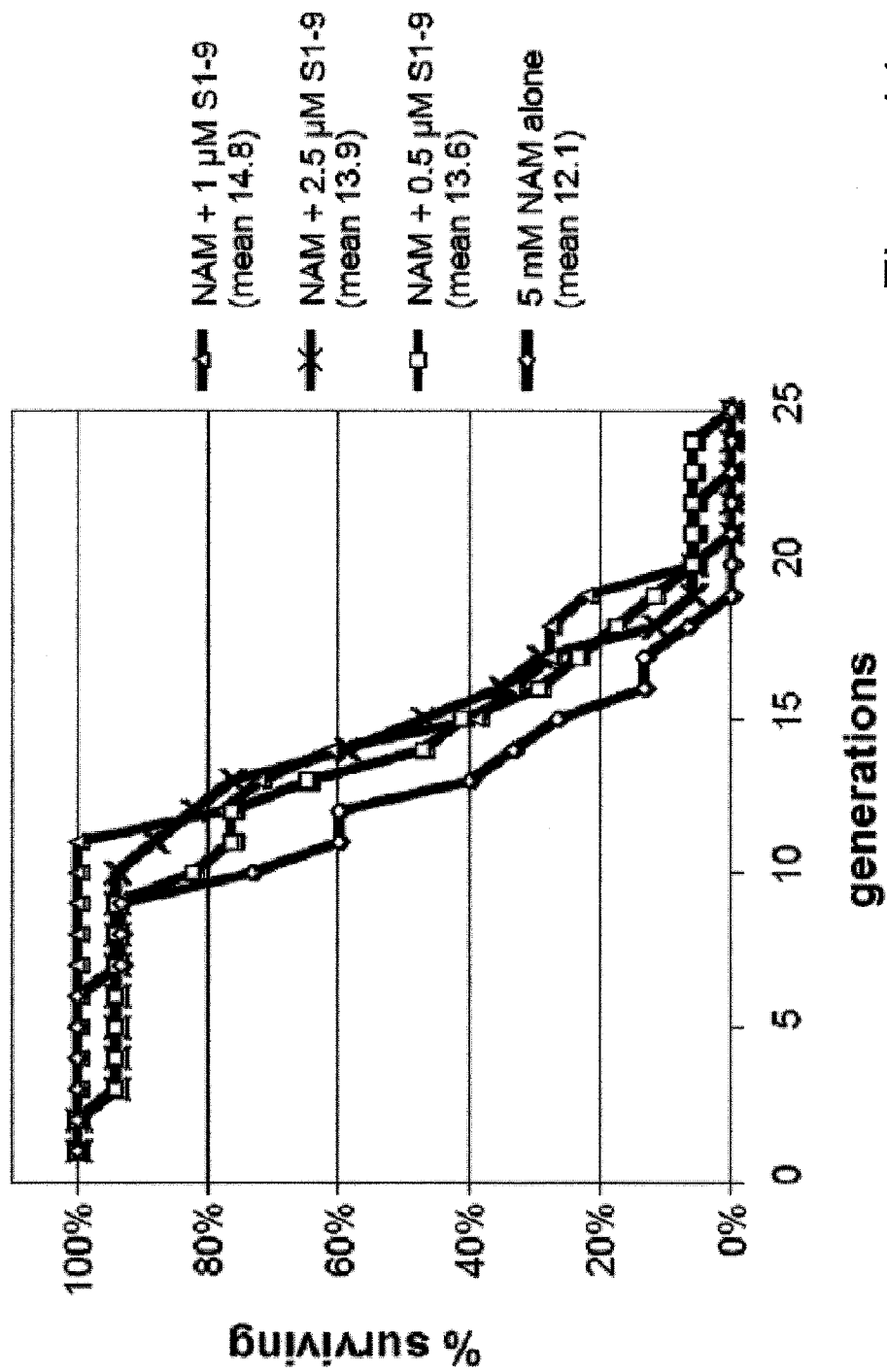
Figure 12:
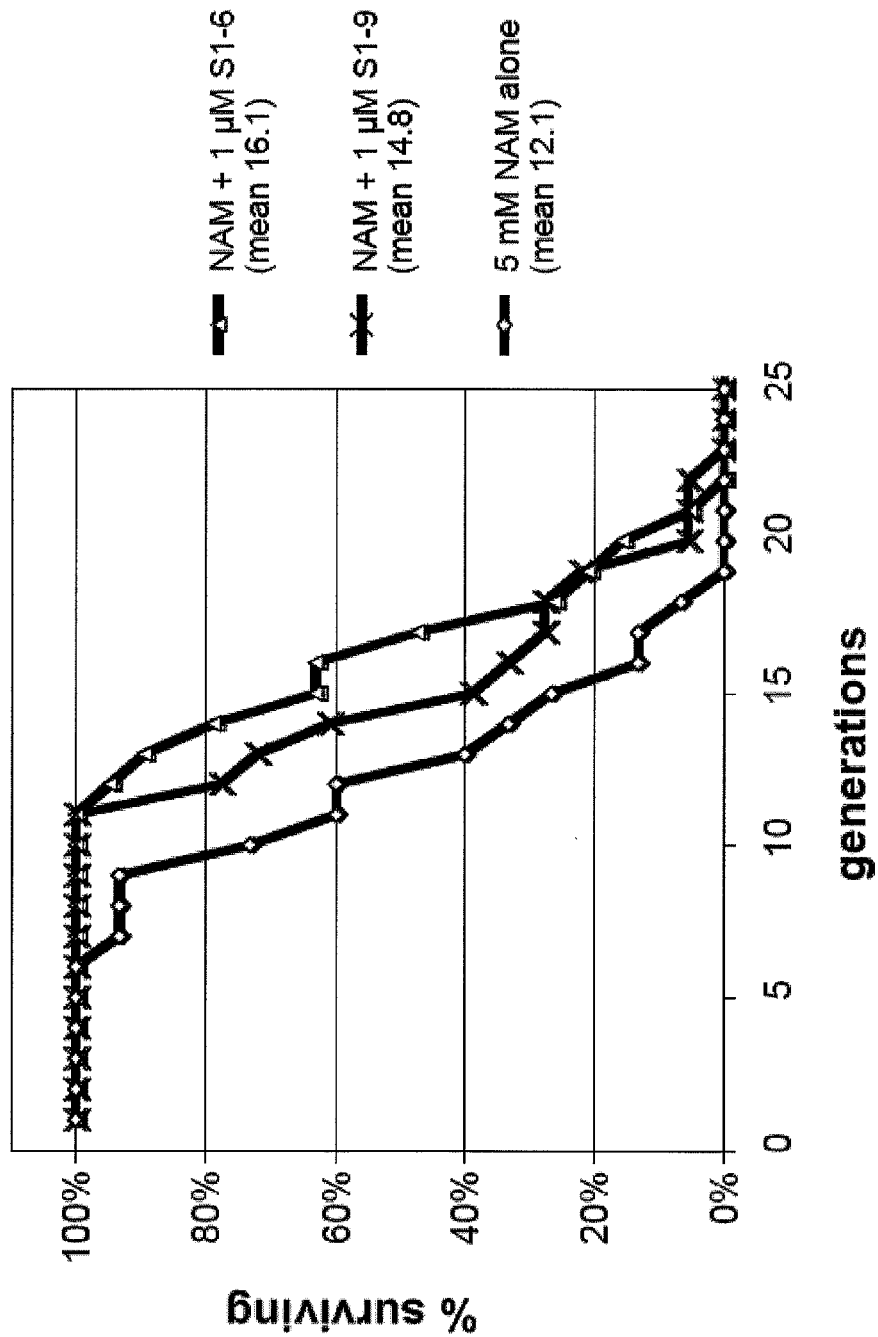
Figure 13:
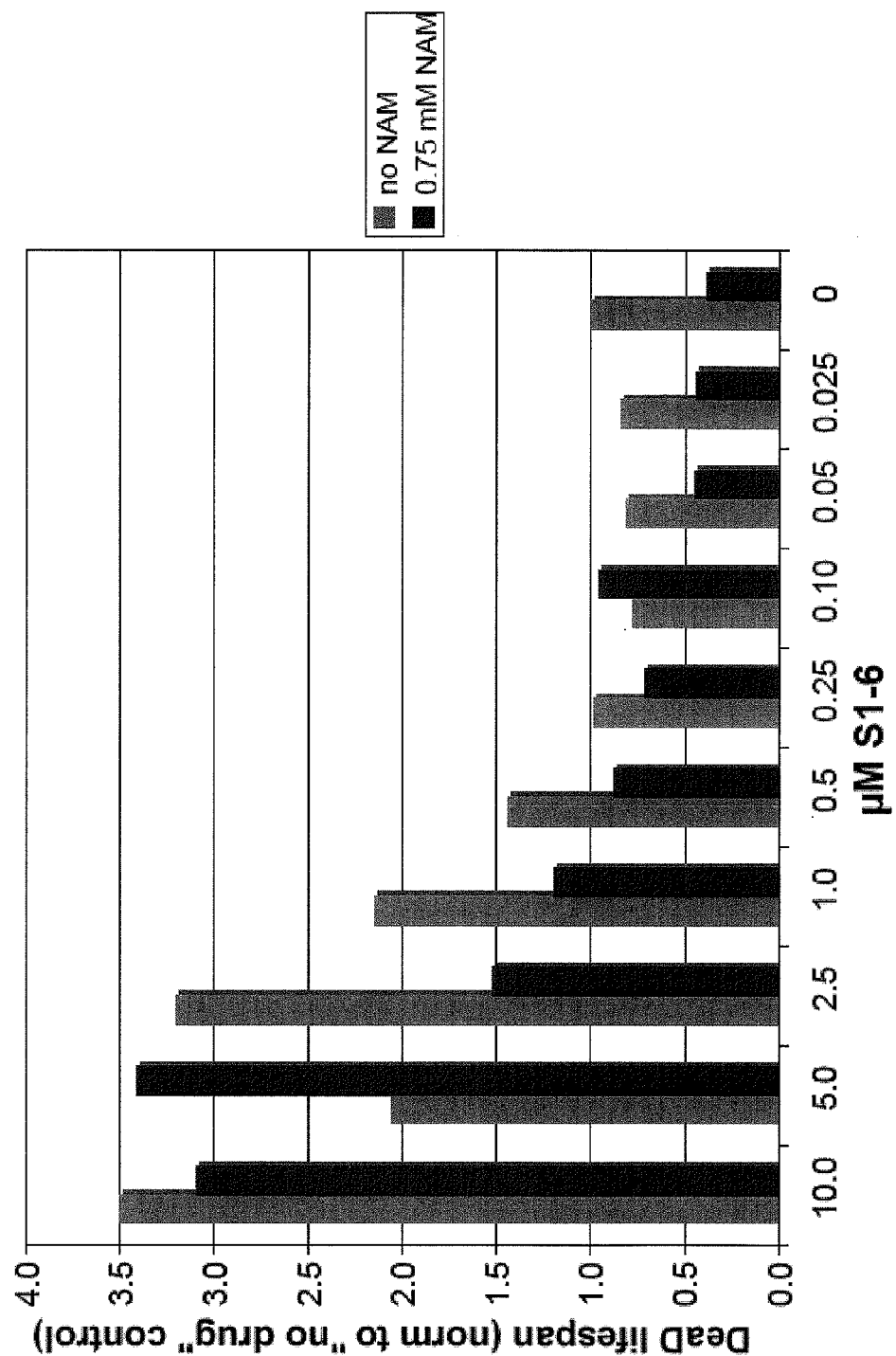
FIGS. 13-14 provide DeaD lifespan assays for a variety of compounds as provided in these Figures.
Figure 14:
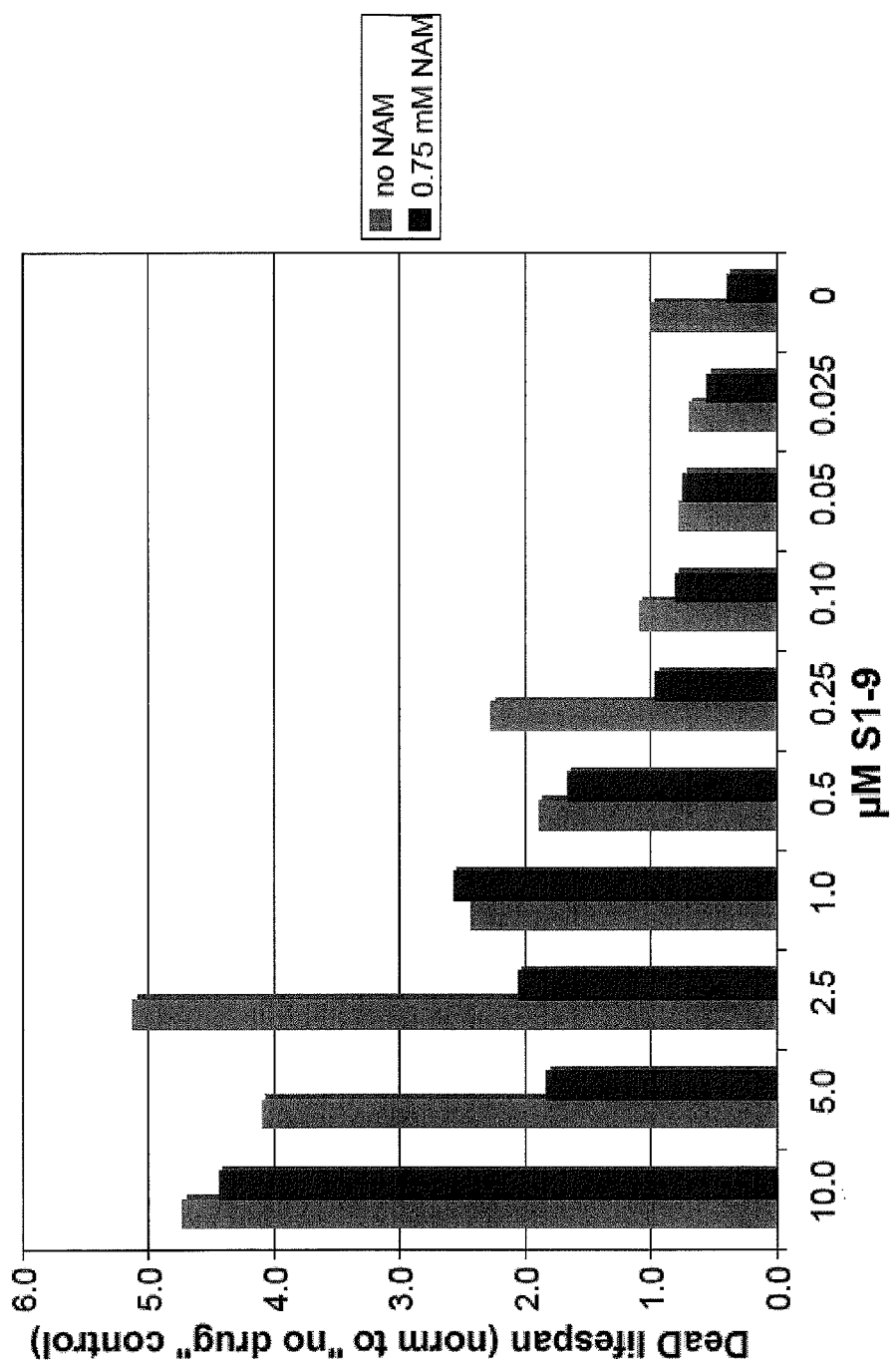

For the DeaD assay results shown in FIGS. 13-14, DeaD assay strain BB579 was grown overnight in SCRaff/Gal (2% raffinose/0.1% galactose) to early log phase and then diluted to an OD600 of 0.0001 in SCD or SCRaff/Gal with or without 0.75 mM nicotinamide and containing the concentration of chemical indicated. Cultures were grown at 30° C. in a Bio-Screen and the OD600 recorded every 20 minutes. DeaD lifespan was calculated by dividing the culture OD600 at 60 hours in SCD by the culture OD600 at 24 hours in SCRaff/Gal, and then normalizing this value to the "no drug" control. For the data of Table 2, the protocol was similar, except that all cultures were in SCD with 0.75 mM nicotinamide, and the OD600 at 60 hours was normalized to the same value for the "no drug" control. For the microdissection assay results of FIGS. 10-12, wild-type strain FY839 was grown overnight in YPGlycerol to mid-log phase and spread on YPD plates containing 5 mM nicotinamide and the concentration of chemical (S1-6 or S1-9) indicated. For each concentration, 20 budded cells were arrayed, and the daughter of each budded cell was moved and became the virgin mother cell for that line. This mother cell was then moved away from her daughter each generation until she ceased to divide, and the number of divisions was recorded (Table 3). Virgin mothers that failed to divide at all, or that could not be separated from their daughter cells, were omitted from the analysis (and are recorded as blanks in Table 3).

Example 11

Assay of Compound 3-11 in Worms

Figure 15:
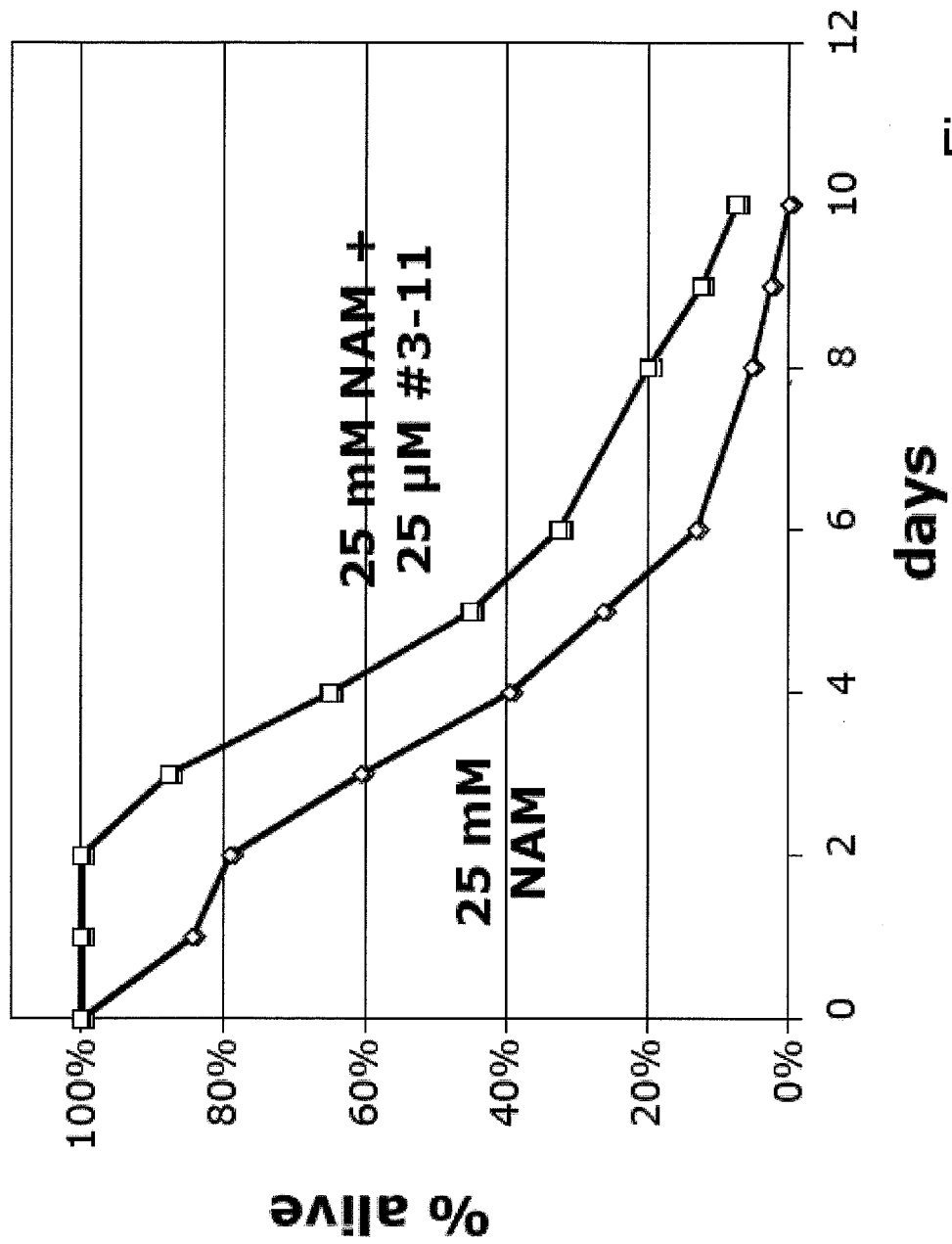
FIG. 15 provides an example of an assay of one of the compounds of the invention (compound 3-11; see Table 2) in *C. elegans*.
Figure 17:
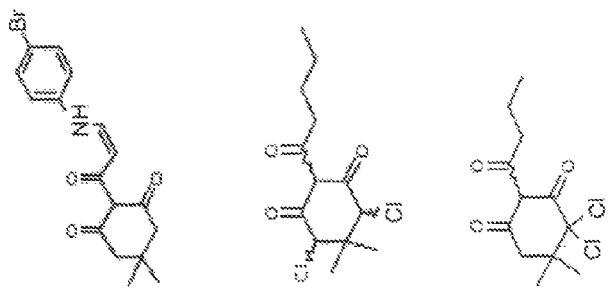
FIG. 17 presents Table 2 which shows examples of commercially available LAC compounds.
Figure 17:
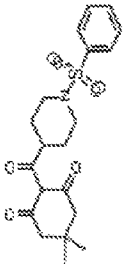
Figure 17:
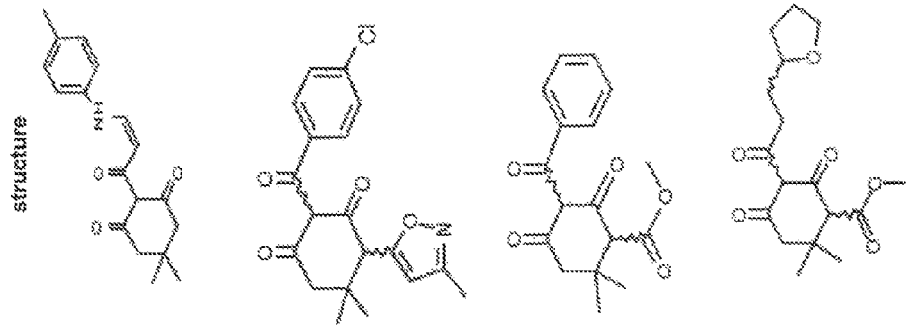
Figure 17:
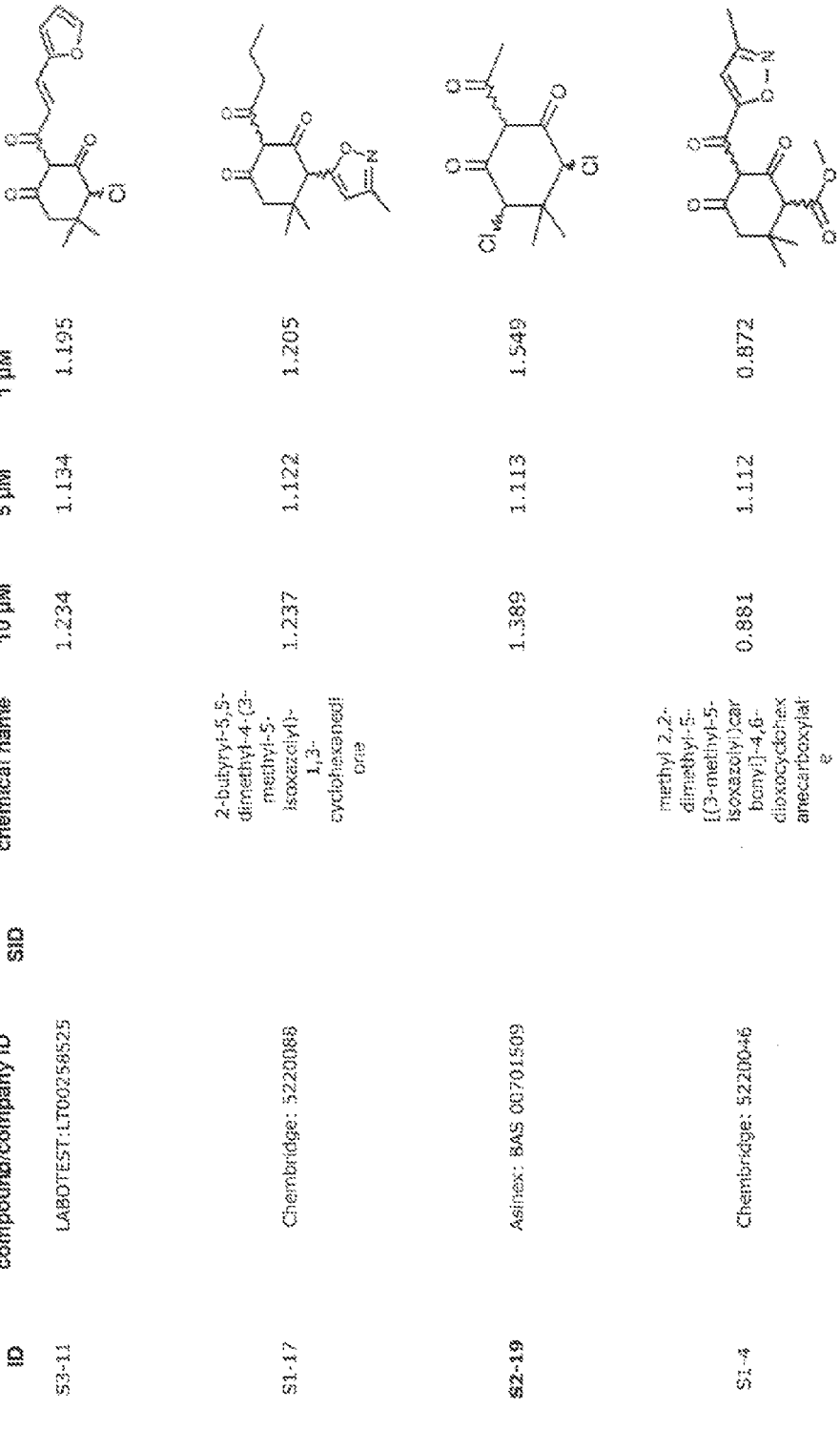
Figure 17:
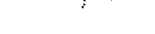
Figure 17:
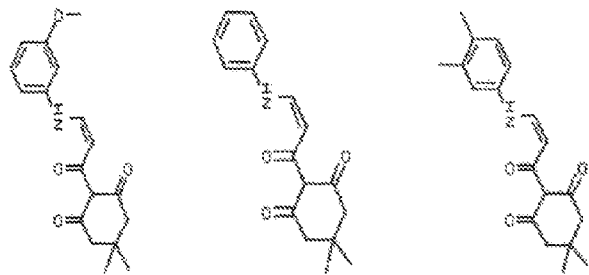

FIG. 15 provides an example of an assay of one of the compounds of the present invention in worms (*C. elegans*), in this case compound 3-11.

The worm *C. elegans* is a powerful system to investigate aging and lifespan. Moreover, as in yeast, NAM has been shown to reduce *C. elegans* lifespan in a Pnc1 and SIR2-ortholog dependent fashion (Van der Horst et al., Mech. Ageing Develop. 128:346-349, 2007). As shown in FIG. 15, compound 3-11, identified using the DeaD assay, reproducibly extends the lifespan of *C. elegans*, partially reversing the lifespan shortening effect of 25 mM NAM in worms. This result is validation that the DeaD assay is capable of discovering small molecules that alter aging and lifespan in metazoan animals like worms. This result dismisses the concern that the DeaD assay might produce results that are only relevant to this fungus. This is demonstrably not the case.

In the present application, the use of the DeaD assay for screening compounds that alter the CR response is described, and data are presented for the results of those screenings.

While specific illustrative embodiments and examples of the present invention have been used to describe the invention in the foregoing, it will be appreciated by those skilled in the art that many equivalents, modifications, substitutions, and variations may be made thereto without departing from the spirit and scope of the invention as defined in the appended claims.

What is claimed is:

1. A method for altering the lifespan of a eukaryotic organism comprising the steps of:
   a) providing a lifespan altering compound comprising scaffold c1:

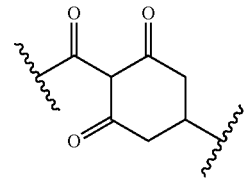 [SMILES: *C(=O)C1C(=O)CC(*)CC1=O]

wherein the compound has an EC50 in a DeaD assay of 10 µM r less if tested in a DeaD assay; and
   b) administering an effective amount of the compound to a eukaryotic organism, such that the lifespan of the eukaryotic organism is altered, wherein the altered lifespan comprises an increase in lifespan.

* * * * *